US008574559B2

(12) United States Patent
Banowski et al.

(10) Patent No.: US 8,574,559 B2
(45) Date of Patent: Nov. 5, 2013

(54) LOW-RESIDUE DEODORANT OR ANTIPERSPIRANT STICK BASED ON AN OIL-IN-WATER DISPERSION/EMULSION

(75) Inventors: Bernhard Banowski, Dusseldorf (DE); Armin Wadle, Erkrath (DE); Marcus Claas, Hilden (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 573 days.

(21) Appl. No.: 11/938,285

(22) Filed: Nov. 11, 2007

(65) Prior Publication Data

US 2008/0241089 A1    Oct. 2, 2008

Related U.S. Application Data

(63) Continuation of application No. PCT/EP2006/004371, filed on May 10, 2006.

(60) Provisional application No. 60/788,022, filed on Mar. 30, 2006, provisional application No. 60/788,028, filed on Mar. 30, 2006.

(30) Foreign Application Priority Data

May 11, 2005  (DE) .................. 10 2005 022 523
Jun. 24, 2005  (DE) .................. 10 2005 029 776
Feb. 1, 2006   (DE) .................. 10 2006 004 957

(51) Int. Cl.
*A61K 8/00*    (2006.01)
*A61K 8/18*    (2006.01)
*A61K 9/00*    (2006.01)
*A61K 8/02*    (2006.01)
*A61Q 15/00*   (2006.01)

(52) U.S. Cl.
USPC ................ 424/65; 424/400; 424/401

(58) Field of Classification Search
USPC ............................ 424/65, 400, 401
See application file for complete search history.

(56) References Cited

U.S. PATENT DOCUMENTS

| 4,205,062 | A |   | 5/1980  | Daahn |
| 4,639,369 | A | * | 1/1987  | Ciaudelli ............... 424/59 |
| 4,704,271 | A |   | 11/1987 | Hourihan et al. |
| 4,725,431 | A |   | 2/1988  | Hourihan et al. |
| 5,466,457 | A |   | 11/1995 | Schneider et al. |
| 5,989,531 | A | * | 11/1999 | Schamper et al. .......... 424/65 |
| 6,007,799 | A |   | 12/1999 | Lee et al. |
| 6,086,887 | A | * | 7/2000  | Parrott ............................ 424/66 |
| 6,383,476 | B1 | * | 5/2002  | Scavone et al. ............... 424/65 |
| 6,428,776 | B1 |   | 8/2002  | Guckenbiehl et al. |
| 6,849,251 | B2 | * | 2/2005  | Banowski et al. ............ 424/65 |
| 2002/0022010 | A1 |   | 2/2002  | Emslie et al. |
| 2002/0054890 | A1 | * | 5/2002  | Gers-Barlag et al. ......... 424/401 |
| 2002/0182233 | A1 | * | 12/2002 | Ambler et al. ................ 424/401 |
| 2003/0103921 | A1 |   | 6/2003  | Brucks et al. |
| 2006/0029624 | A1 | * | 2/2006  | Banowski et al. ............ 424/401 |

FOREIGN PATENT DOCUMENTS

| CA | 2373504      | 11/2000 |
| DE | 2335549      | 2/1995  |
| DE | 19643238     | 4/1998  |
| DE | 19749819     | 5/1999  |
| DE | 19832425     | 1/2000  |
| DE | 19962878     | 6/2001  |
| DE | 19962881     | 6/2001  |
| DE | 10333245     | 7/2005  |
| DE | 102004011968 | 9/2005  |
| EP | 0281288      | 9/1988  |
| EP | 0291334      | 11/1988 |
| EP | 0617952      | 10/1994 |
| WO | WO9424997    | 11/1994 |
| WO | WO9817238    | 4/1998  |
| WO | WO9959537    | 11/1999 |
| WO | WO0067713    | 11/2000 |
| WO | WO0217870    | 3/2002  |
| WO | WO0232914    | 4/2002  |
| WO | WO02083091   | 10/2002 |

OTHER PUBLICATIONS

C. D. Vaughan, Cosmetic & Toiletries, vol. 103, Oct. 1988, pp. 47-69.
I.H. Derby et al., Journal American Chemical Society., vol. 38, (1916), pp. 1442-1473.
Journal American Chemical Society., vol. 38, (1916) p. 321.
H. Janistyn, Handbuch der Kosmetika und Riechstoffe, Hüthig-Verlag, Heidelberg, 3. Edition, (1978), vol. 1, p. 470.
H. Janistyn, Handbuch der Kosmetika und Riechstoffe, Hüthig-Verlag, Heidelberg, 3. Edition, (1978), vol. 3, pp. 68-78.

* cited by examiner

*Primary Examiner* — Mina Haghighatian
*Assistant Examiner* — Luke Karpinski
(74) *Attorney, Agent, or Firm* — David LeCroy; Ryan Fortin; Krista A. Kostiew

(57) ABSTRACT

Deodorant or antiperspirant sticks based on an oil-in-water dispersion/emulsion for application on the skin.

18 Claims, No Drawings

LOW-RESIDUE DEODORANT OR ANTIPERSPIRANT STICK BASED ON AN OIL-IN-WATER DISPERSION/EMULSION

CROSS-REFERENCE TO RELATED APPLICATIONS

This application is a continuation under 35 U.S.C. §365(c) and 35 U.S.C. §120 of International Application No. PCT/EP2006/004371, filed May 10, 2006. This application also claims priority under 35 U.S.C. §119 of U.S. Provisional Application Nos. 60/788,022 and 60/788,028, both filed Mar. 30, 2006. This application also claims priority under 35 U.S.C. §119 of German Patent Application Nos. 10 2005 022 523.3, filed May 11, 2005, 10 2005 029 776.5, filed Jun. 24, 2005 and 10 2006 004 957.8, filed Feb. 1, 2006. The International Application, the two United States Provisional Applications and the three German Applications are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to a deodorant or antiperspirant stick based on an oil-in-water dispersion/emulsion for the application of water-soluble active ingredients to the skin.

(2) Description of Related Art, Including Information Disclosed Under 37 C.F.R. §§1.97 and 1.98

Standard commercial deodorants and antiperspirants are mostly formulated as sprays or as sticks; there are also roll-on preparations and creams in the market. Many stick antiperspirant preparations are formulated as anhydrous suspension sticks. Preparations of this type leave behind a pleasant dry feel on the skin for the user following application. However, effective release of the water-soluble antiperspirant active ingredients from such preparations is limited (cf.: Chemistry and Technology of the Cosmetics and Toiletries Industry, edition D. F. Williams and W. H. Schmitt, London: Blackie, 1996, 2nd edition, p. 326), and in most cases the feeling of freshness valued by many consumers is not achieved. The anhydrous preparations, in particular those based on volatile silicone oils, have the disadvantage that the dispersed active ingredients readily lead to visible product residues on skin and clothing. Furthermore, such preparations are relatively expensive since the oil components are more expensive as active ingredient carriers than water. Compression during application often results in the loss of oil, which reduces the cosmetic acceptance of these preparations for the user.

Compared with anhydrous sticks, as are known, for example, from WO 94/24997 A1 and WO 00/67713 A1, emulsion sticks, as are disclosed, for example, in WO 98/17238 A1, EP 281 288 A2, DE 2 335 549, U.S. Pat. No. 4,725,431, EP 617 952 A1 and EP 291 334, have a number of advantages. Replacing the wax and oil additives with water makes the emulsion sticks more cost-effective to manufacture. The emulsified waxes convey a soft, gentle feel on the skin, and, finally, water-soluble cosmetic active ingredients (i.e., in particular, antiperspirant active ingredients) can more readily be released onto the skin since they are already present in dissolved form in the aqueous phase of the emulsion.

WO 02/017870 A2 discloses antiperspirant sticks without a W/O emulsifier or high melting wax which contain a siliconized polyamide as a consistency regulator or structurant. According to patent claim 1 of WO 02/017870 A2, the hydrous phase forms the internal phase, i.e., the dispersed phase, and the gels disclosed are water-in-oil emulsions.

WO 02/032914 A1 discloses, with reference to several exemplifying embodiments, hydrous antiperspirant sticks based on a water-in-oil emulsion which contain acylated cellobiose as the consistency regulator or structurant and contain a high fraction of the silicone and hydrocarbon oils which are unfavorable according to the invention, and furthermore do not contain oil-in-water emulsifiers or a high melt wax.

Since the emulsion sticks of the cited prior art are formulated on the basis of a water-in-oil dispersion/emulsion, the water-soluble active ingredients are present in the inner, dispersed phase and, following application, must first migrate through the outer, lipophilic layer in order to reach their site of action on the skin. The known water-in-oil emulsion sticks thus have disadvantages which are similar to those of anhydrous suspension sticks with regard to the availability of active ingredient.

DE 19749819 A1 discloses water-containing and oil-containing, wax-free antiperspirant sticks based on an oil-in-water emulsion. Sticks of this type have inadequate cosmetic properties, leave behind unpleasant sticky and visible residues and exhibit a stability which is insufficient for prolonged use. One example with glycerol monostearate as W/O emulsifier and octyldodecanol as oil component has a medium-firm consistency and a greasy feel on the skin and begins to soften at just 50° C.

WO 99/59537 A1 discloses hydrous cosmetic sticks which comprise wax components with a melting point of >50° C., nonionic water-in-oil emulsifiers, a nonionic oil-in-water emulsifier with an HLB value of more than 7 and a polyol. Some of the sticks contain oils which are liquid at 25° C. but which, instead of being incorporated at the beginning of the emulsion process as in the sticks of the present application, are stirred in as a pre-emulsified concentrate, for instance a micro-emulsion or PIT emulsion, during the cooling phase of the stick mass at a temperature of 55° C. This type of production method is needed in order not to endanger or even destroy the stability of the system for a dispersion of lipid and wax crystals. Sticks of this type likewise have inadequate cosmetic properties, can leave behind unpleasant sticky and visible residues, and exhibit a stability which is inadequate for prolonged use.

WO 02/083091 A1 discloses structured antiperspirant compositions in the form of a microemulsion which represents an oil-in-water microemulsion or a water-in-oil microemulsion or a bicontinuous phase, depending on the kind and quantity of surfactants, but in which the bicontinuous phase predominates overall. The (transparent) microemulsions are condensed by an oil-soluble or oil-dispersible "structurant." The oil-soluble or oil-dispersible "structurant" is chosen from among esters and amides of 12-hydroxystearic acid, esters and amides of di- and tricarboxylic acids, sterols, sterol esters such as oryzanol, cellobiose fatty acid esters, sugar esters such as acylated maltose, and non-crosslinked oil-soluble or oil-dispersible polymer oil phase condensing agents such as the commercial product Kraton G. Ionic emulsifiers with an HLB value from 2-15, preferably with an HLB value under 12, are also incorporated. Polyols are disclosed as optional only. This document does not disclose the possible significance of the solubility parameters of W/O emulsifiers and oil components being matched with one another. The structural difference between these compositions and the oil-in-water dispersion/emulsion sticks of the present invention, which are not microemulsions, becomes particularly clear because of the high fraction, namely 19-66% by weight relative to the overall composition, of silicone and (paraffinic) hydrocarbon oils which all exemplifying embodiments disclose but which are unfavorable according to the invention.

Published Application Nos. DE 199 62 878 A1 and DE 199 62 881 A1 disclose deodorant or antiperspirant creams based on an oil-in-water emulsion which have, at 21° C., a viscosity of at least 50,000 mPas, preferably in the range from 200,000-1,500,000 mPas, i.e., they are in viscous to highly viscous paste form. These creams comprise wax components with a melting point of >50° C., nonionic water-in-oil emulsifiers, but not an ethylene glycol ester or a pentaerythryl ester, nonionic oil-in-water emulsifiers with an HLB value of more than 7, and a polyol. Being soft creams, they can be applied either by using only the fingers, which is rejected by many consumers as being impractical, or by pouring the creams into special applicators, which are significantly more expensive than the stick sheaths for the deodorant or antiperspirant sticks according to the invention. If, after being heated and mixed, the compositions disclosed in DE 199 62 878 A1 and DE 199 62 881 A1 were cooled statically, i.e., without stirring, then stick-like compositions would be obtained which have overall unfavorable application properties, such as poor haptics and/or inadequate stability, for example, as a result of phase separation or the formation of water condensation, since the emulsifiers and the oils are not matched to one another as in the present invention.

DE 10 2004 036 689.6 was not published before the filing date of DE 10 2005 002523.3, from which this application claims priority. DE 10 2004 036 689.6 discloses deodorant or antiperspirant sticks in the form of an oil-in-water dispersion containing at least one lipid or wax component with a melting point of >50° C., at least one nonionic oil-in-water emulsifier with an HLB value above 7 within a nonionic oil-in-water emulsifier system with an average HLB value between 10 and 19; as a consistency regulator and/or water binder, at least one nonionic water-in-oil emulsifier with an HLB value of greater then 1.0 and less than/equal to 7.0, which can form liquid crystalline structures with water alone or with water in the presence of a hydrophilic emulsifier, and at least one oil which is in a liquid state at 20° C. and is not a fragrance component or essential oil--the maximum deviation between the (average) solubility parameter of all the constituent oils and the (average) solubility of the water-in-oil emulsifier or emulsifiers being $-0.7$ $(cal/cm^3)^{0.5}$ or $+0.7$ $(cal/cm^3)^{0.5}$ in the presence of linear saturated fatty alcohol as the water-in-oil emulsifier or part of a water-in-oil emulsifier, respectively, and $-0.4(cal/cm^3)^{0.5}$ or $+0.7$ $(cal/cm^3)^{0.5}$ in the presence of water-in-oil emulsifiers other than linear saturated fatty alcohols in the absence of linear saturated fatty alcohols as a water-in-oil emulsifier, respectively; at least one water-soluble polyhydric $C_2$-$C_8$ alkanol with 2-6 hydroxyl groups and/or at least one water-soluble polyethylene glycol with 3-20 ethylene oxide units; 5% to less than 50% by weight of water relative to the whole composition; and at least one deodorant or antiperspirant agent; where the stick exhibits a penetration force value in the range of 200-600 gram-force (g-force) at a depth of 5.000 mm (five millimeters) and a maximum electrical resistance of 300 kΩ(Kiloohm). It has been discovered, however, that glycerol monostearate and glycerol distearate, the preferred W/O emulsifiers in DE 10 2004 036 689.6, can present difficulties with respect to large-scale production, particularly as concerns product consistency.

BRIEF SUMMARY OF THE INVENTION

Therefore, the object was to develop a deodorant or antiperspirant composition which is suitable as an effective carrier for water-soluble active ingredients and permits the rapid release of the active ingredient on the skin.

A further object was to develop a deodorant or antiperspirant composition with excellent cosmetic care properties.

A further object was to develop a deodorant or antiperspirant stick which, on the one hand, has high stability, i.e., solidity, but on the other hand, has a pleasant release behavior, i.e., is not too solid but can be readily spread over the skin and in so doing releases an adequate amount of product.

A further object was to develop a deodorant or antiperspirant composition which, when applied to the skin, leaves behind as little sticky or visible residue as possible.

A further object was to develop a deodorant or antiperspirant composition which leaves behind optimally little visible residue on clothing which comes into contact with the treated skin.

A further object was to develop a deodorant or antiperspirant composition which can be readily washed off of the skin.

A further object was to develop a deodorant or antiperspirant composition with a cost-performance ratio which is favorable economically and in terms of application.

A further object was to develop a deodorant or antiperspirant composition which allowed for the mass production of stable deodorant or antiperspirant sticks with a suitable consistency.

Surprisingly and unforeseeably to the person skilled in the art, these objects were achieved through a deodorant or antiperspirant stick in the form of an oil-in-water dispersion/emulsion comprising:

a) at least one lipid or wax component with a melting point of >50° C. which is not included in components b) or c);

b) at least one nonionic oil-in-water emulsifier with an HLB value of more than 7 within an oil-in-water emulsifier mixture with an average HLB value in the range of 10-19;

c) at least one nonionic water-in-oil emulsifier with an HLB value greater than 1.0 and less than or equal to 7.0, chosen from among the monoesters and diesters of ethylene glycol and the mono-, di-, tri-, and tetraesters of pentaerythritol with linear saturated and unsaturated fatty acids having 12-30, but especially 14-22, carbon atoms which can be hydroxylated, and mixtures thereof as a consistency regulator and/or water binder;

d) at least one oil which is in a liquid state at 20° C. and is not a fragrance component or essential oil, in which the maximum deviation between the (average) solubility parameter of all the constituent oils d) and the (average) solubility parameter of the water-in-oil emulsifier or emulsifiers is $-0.7$ $(cal/cm^3)^{0.5}$ or $+0.7$ $(cal/cm^3)^{0.5}$, respectively, in the presence of linear saturated fatty alcohols with a chain length of at least 8 carbon atoms and $-0.4$ $(cal/cm^3)^{0.5}$ or $+0.7$ $(cal/cm^3)^{0.5}$, respectively, in the presence of water-in-oil emulsifiers other than linear saturated fatty alcohols with a chain length of at least 8 carbon atoms, linear saturated fatty alcohols with a chain length of at least 8 carbon atoms being absent;

e) at least one water-soluble polyhydric $C_2$-$C_8$-alkanol with 2-6 hydroxyl groups and/or at least one water-soluble polyethylene glycol with 3-20 ethylene oxide units;

f) 5% to less than 50% by weight of water, relative to the overall composition; and g) at least one deodorant or antiperspirant active ingredient.

BRIEF DESCRIPTION OF THE SEVERAL VIEWS OF THE DRAWING(S)

Not Applicable

DETAILED DESCRIPTION OF THE INVENTION

The lipid or wax component with a melting point of >50° C. forms a gel matrix with the oil(s) and optionally further higher-melting lipid or wax components; this gel matrix can absorb larger amounts of water and polyol. These structures, which are stabilized by certain amounts of water-in-oil emulsifiers and oil-in-water emulsifiers, leave behind a fresh, cooling impression upon application due to their water content. Here, the emulsifiers are matched to one another so that the stick compositions according to the invention are present in the form of an oil-in-water dispersion/emulsion. The stick compositions of the invention are thus not present as a microemulsion. To produce the stick compositions of the invention, the water phase and the oil phase must be heated to at least 70° C. and stirred together or homogenized while hot, i.e., at least at 70° C., in order to achieve the emulsion structure of the invention. A production method like the one disclosed in U.S. Pat. No. 4,205,062 (kneading of fat and water phase at 65° C.), for example, is inadequate to obtain a homogenous stick composition based on an oil-in-water dispersion/emulsion. Without wishing to be bound to this theory, it is assumed that the oil-in-water emulsifiers, together with some of the water-in-oil emulsifiers, form lamellar liquid crystal phases, which are built up with some of the water into a hydrophilic gel phase. This hydrophilic gel phase surrounds the aqueous bulk phase. Dispersed within this aqueous bulk phase are, in turn, the lipophilic components, surrounded by a lipophilic gel phase, which is formed by the water-in-oil emulsifiers with some of the oil-in-water emulsifiers and some water.

The antiperspirant active ingredient is dissolved in the outer, continuous aqueous phase, resulting in a considerably improved and more efficient active ingredient release compared to the known anhydrous suspension sticks and water-in-oil emulsion sticks. The O/W emulsion basis of the stick compositions of the invention results in a considerably improved and more efficient active ingredient release compared to the known anhydrous suspension sticks and water-in-oil emulsion sticks. This active ingredient release can be determined indirectly very readily by measuring the electrical resistance of the particular product. Measuring the electrical resistance of such compositions is also a suitable way to be able to distinguish between an oil-in-water system and a water-in-oil system. An oil-in-water system exhibits a high electrical conductivity and therefore a low electrical resistance owing to the continuous water phase. The precise measurement set-up and the measurement procedure are described below (see below). The sticks according to the invention accordingly have an electrical resistance of at most 300 kΩ, preferably of at most 100 kΩ, and particularly preferably of at most 80 kW. In contrast, the sticks disclosed in WO 98/17238 A1 exhibit an electrical resistance of more than 3,000 kΩ; therefore, they obviously employ a water-in-oil system.

The solidification of the deodorant or antiperspirant sticks according to the invention does not take place on the basis of soap gels or fatty acid salt gels, fatty acids being understood as meaning alkanoic, alkenoic and alkinoic acids having at least 4 carbon atoms, which can be substituted, for example, by hydroxyl groups. In a particularly preferred embodiment, the deodorant or antiperspirant sticks according to the invention are free of soap gels or fatty acid salt gels, in particular, free of lithium, sodium, potassium, ammonium, diethanolamine and triethanolamine salts of fatty acids. Sticks on a soap base are incompatible with acidic antiperspirant active ingredients such as are used in the antiperspirant sticks of the invention.

The solidification of the deodorant or antiperspirant sticks according to the invention does not take place on the basis of inorganic and/or organic polymeric hydrogel formers, such as celluloses, cellulose derivatives, for example, hydroxyalkylcelluloses, polyacrylates, veegum or bentones. In a particularly preferred embodiment, the deodorant or antiperspirant sticks according to the invention are free of gels formed by inorganic and/or organic polymeric hydrogel formers.

In addition to the favorable active ingredient release, the formulation as oil-in-water dispersion/emulsion is accompanied by further advantages. First, the composition can be readily washed off of the skin. Second, during or following application to the skin, a therapeutic oil-in-water cream forms together with the skin moisture.

Surprisingly and unexpectedly to the person skilled in the art, it has been found that the oil components and the water-in-oil emulsifier or the water-in-oil emulsifier mixture have to be matched to one another with regard to their solubility parameters in order to form stick compositions with satisfactory performance-related hardnesses. For a definition of the solubility parameter within the meaning of the present invention, reference is made to the publication "Solubility—Effects in Product, Package, Penetration and Preservation," by Chr. D. Vaughan in Cosmetics & Toiletries, vol. 103, October 1988, pages 47-69. The values for the solubility parameters published therein are noted in the non-SI unit $(cal/cm^3)^{0.5}$. For the sake of simplicity, this non-SI unit will be retained in this specification. The values can be easily converted based on the relation 1 cal=4,1860 Joules.

A number of the solubility parameters tabulated by Vaughan in Cosmetics & Toiletries, Vol. 103, October 1988, pages 47-69, were calculated according to the Hildebrand equation (see C. D. Vaughan: J. Soc. Cosmet. Chem., Vol. 36, pp. 319-333 (September/October 1985) and the Hildebrand equation cited therein, and J. Am. Chem. Soc., Vol. 38, pages 1442-1473 (1916) and J. Hildebrand and R. Scott: The Solubility of Nonelectrolytes, 3rd Edition, Reinhold Publ. Corp., New York, 1949); they are summarized below. Vaughan mentions that the solubility parameters can be calculated not only using the Hildebrand equation but also, for example, based on the evaporation enthalpy (Scatchard, J. Am. Chem. Soc., Vol. 38, page 321 (1916)). All the calculation methods can produce different values for the solubility parameters, especially if the chemical material has an acid or base function.

In the present invention, it is preferable when the matching of the solubility parameters of the oil components and the water-in-oil emulsifier or the water-in-oil emulsifier mixture is performed only for solubility parameter values that were calculated using the same method. It is particularly preferred when the solubility parameter values that were calculated using the Hildebrand equation ((see C. D. Vaughan: J. Soc.

Cosmet. Chem., Vol. 36, pages 319-333 (September/October 1985)) are used for the matching according to the invention. If there is no available pair of solubility parameter values that were determined using the same method for a particular combination of oil component and water-in-oil emulsifier, it is also possible to use values that were determined using different methods, even experimental ones. However, that is a less preferred alternative according to the invention.

TABLE 1

Solubility of Various Chemical Components.
(from Cosmetics & Toiletries, Vol. 103, October 1988, pages 47-69)

| MATERIAL NAME (CTFA) with Dielectric Constant | Solubility Parameter $(cal/cm^3)^{0.5}$ | Ref. |
|---|---|---|
| Helium (1.06) | 0.50 | * N |
| Hydrogen (1.23) | 2.50 | * N |
| Propellant 13 | 2.59 | * O |
| Methane (1.70) | 4.70 | * O |
| Neon | 4.90 | * N |
| Perfluorohexane | 5.68 | A |
| Perfluoroctane | 5.72 | A |
| Cyclomethicone D5 (2.50) | 5.77 | MO |
| Nitrogen (1.45) | 5.90 | * N |
| Dimethicone | 5.92 | * O |
| Cyclomethicone D4 (2.39) | 5.99 | MO |
| Squalane | 6.03 | MO |
| Propellant 12 (2.13) | 6.11 | * O |
| Hexamethyldisiloxane (2.17) | 6.15 | MO |
| Isocetyl Stearate | 6.19 | M |
| Squalene | 6.19 | MO |
| Polytetrafluoroethylene | 6.20 | * |
| Propane | 6.21 | * O |
| Propellant 22 (6.11) | 6.23 | MO |
| Perfluorodecalin | 6.34 | A |
| Neopentane | 6.38 | CO |
| Safflower Oil | 6.42 | L1 |
| Melene (C30) | 6.58 | C |
| Docosane (C22) | 6.60 | I |
| Almond Oil | 6.81 | L1 |
| Cyclohexane (2.02) | 7.30 | E |
| Dioctyl Ether | 7.30 | A |
| Eicosane (020) | 7.32 | C |
| Lanolin Oil | 7.33 | L1 |
| Petrolatum | 7.33 | * O |
| Bethenic Acid | 7.35 | I0 |
| Diethyl Ether (4.34) | 7.37 | CO |
| Corn Oil-Refined | 7.40 | L1 |
| Cetane (016) | 7.41 | I |
| Heptane (1.92) | 7.41 | CO |
| Isostearyl Neopentanoate | 7.43 | M |
| Octyl Palmitate | 7.44 | 0 |
| Propyl Fluoride | 7.48 | C |
| Rice Oil - SO | 7.48 | L1 |
| Tridecane (C13) | 7.48 | CO |
| Propellant 11 (2.28) | 7.49 | 0 |
| Cottonseed Oil | 7.52 | L1 |
| Carbon Dioxide (1.60) | 7.53 | H |
| Isopropyl Linoleate | 7.55 | M |
| Cod Liver Oil | 7.56 | L1 |
| Erucic Acid | 7.57 | CO |
| Octane (1.95) | 7.58 | MO |
| Cetyl Octanoate | 7.59 | M |
| Decene-1 | 7.59 | C |
| Dodecene (2.01 (7.65-I) | 7.59 | C |
| Diethylhexyl Adipate | 7.60 | M |
| Decane (1.99) | 7.62 | CO |
| C12-15 Alcohols Benzoate | 7.63 | MO |
| Isopentane | 6.82 | CO |
| Avocado Oil | 6.83 | L1 |
| Nonacosane (D29) | 6.83 | C |
| Arachidic Acid | 6.85 | H |
| Pristane | 6.85 | MO |
| Decyl Oleate | 6.92 | M |
| Cl-Isoparaffin (1.94) | 6.93 | MO |
| Diisopropyl Ether (3.88) | 6.95 | KE |
| Argon (1.53) | 7.00 | * N |

TABLE 1-continued

Solubility of Various Chemical Components.
(from Cosmetics & Toiletries, Vol. 103, October 1988, pages 47-69)

| MATERIAL NAME (CTFA) with Dielectric Constant | Solubility Parameter $(cal/cm^3)^{0.5}$ | Ref. |
|---|---|---|
| Sperm Oil | 7.09 | * O |
| White Mineral Oil | 7.09 | * O |
| Pentane | 7.10 | * O |
| Tricosane (C23) | 7.13 | C |
| Isodecyl Oleate | 7.17 | M |
| Propellant 113 | 7.19 | H |
| Oxygen (1.50) | 7.20 | * N |
| Cholesteryl Oleate | 7.24 | * |
| Peanut Oil | 7.74 | L1 |
| Hexane (1.88) | 7.28 | CO |
| Linseed Oil | 7.29 | * O |
| Octadecane (C18) | 7.29 | C |
| Isopropyl Myristate | 8.02 | 0 |
| Turpentine (pinene) (2.70) | 8.03 | CO |
| Human Erythrocute | 8.05 | * |
| Methyl Oleate (3.21) | 8.05 | CO |
| Cetyl Acetate | 8.06 | 0 |
| Methyl Linoleate | 8.08 | C |
| Isostearic Acid | 8.09 | 0 |
| Coconut Oil | 8.10 | L1 |
| Myristic Acid (C14) | 8.10 | I0 |
| Dibutylamine | 8.15 | * |
| Eucalyptol (Cineole) | 8.17 | L1 |
| Natural Rubber | 8.20 | H |
| Octylamine | 8.21 | A |
| Isobutyl Stearate | 7.65 | 0 |
| Butyl Myristate | 7.68 | D |
| Butyl Stearate (3.11) | 7.68 | CO |
| Stearic Acid (C18) (2.30) | 7.74 | I0 |
| Dioctyl Maleate | 7.75 | 0 |
| Octyl Fluoride | 7.76 | AG |
| Isopropyl Palmitate | 7.78 | 0 |
| Dioctyl Adipte | 7.82 | M |
| Oleth-3 | 7.83 | * O |
| Diethyl Amine | 7.86 | C |
| Linolenic Acid | 7.86 | C0 |
| Olive Oil | 7.87 | * O |
| Palmitic Acid (C16) (22.30) | 7.89 | I0 |
| Oleic Acid (2.46) | 7.91 | I0 |
| PEG-4 Stearate | 7.92 | 0 |
| Tetraethyl Lead | 7.92 | E |
| Tridecyl Neopentanoate | 7.92 | L1 |
| Pentaerythrityl Tetraoleate | 7.98 | L1 |
| Tocopheryl Acetate | 7.98 | M |
| Ethyl Myristate | 8.00 | C |
| Stearyl Alcohol (C18) | 8.90 | I0 |
| Methyl Hexyl Ketone | 8.91 | A |
| Octyl Dodecanol | 8.92 | OM |
| Butyl Acetate (5.01) | 8.93 | CO |
| Cetyl Alcohol (CIG) | 8.94 | I0 |
| alpha-Thujone | 8.94 | A |
| Toluene (2.38) | 8.94 | C |
| Oleyl Alcohol | 8.95 | CO |
| Propylene Oxide | 8.99 | A |
| *Aspergillus Niger* | 9.00 | P |
| Octyl Dimethyl PABA 9.34 G | 9.01 | OM |
| Propyl Acetate | 9.02 | CO |
| Chloroform | 9.05 | A |
| Propylene Glycol Dipelargonate | 8.21 | L1 |
| Titanium Isopropoxide | 8.21 | M |
| Melissyl Alcohol (C30) | 8.22 | CO |
| Glycol Distearate | 8.24 | J3 |
| Glycol Stearate | 8.28 | J3 |
| Capric/Caprylic Triglycerid | 8.29 | L1 |
| Isosteareth-2 | 8.29 | L1 |
| PPG-2 Myristyl Ether | 8.29 | L1 |
| Ricinoleic Acid | 8.30 | C |
| *Staphylococcus Aureus* | 8.30 | P |
| Glyceryl Isostearate | 8.31 | J3 |
| Glyceryl Stearate (mono) | 8.31 | * O |
| Laureth-4 | 8.31 | J3 |
| Limone (2.30) | 8.33 | C |
| Propylene Glycol Laurate | 8.33 | L1 |

TABLE 1-continued

Solubility of Various Chemical Components.
(from Cosmetics & Toiletries, Vol. 103, October 1988, pages 47-69)

| MATERIAL NAME (CTFA) with Dielectric Constant | Solubility Parameter $(cal/cm^3)^{0.5}$ | Ref. |
|---|---|---|
| Octyl Mercaptan | 8.35 | K |
| PEG-2 Stearate | 8.36 | J3 |
| Ethyl Caprate (C10) | 8.39 | A |
| Radon | 8.40 | * N |
| Amyl Acetate | 8.43 | C |
| Glyceryl Stearate SE | 8.43 | J3 |
| Diisopropyl Adipate | 8.46 | E0 |
| Lauric Acid (C12) | 8.46 | I0 |
| Polyethylene (2.35) | 8.50 | * 0 |
| Diisopropyl Amine | 8.51 | * 0 |
| Polyglyceryl-3 Oleate | 8.52 | J3 |
| Ethylene/Vinyl Acetate (AC400) | 8.55 | * 0 |
| Ethyl Caprylate (C8) | 8.57 | A |
| Octyl Acetate | 8.58 | A |
| Octyl Iodide | 8.58 | A |
| Ethyl Oleate (3.17) | 8.60 | * |
| Isopropylbenzene (12.38) | 8.60 | * |
| Sorbitan Laurate | 8.61 | 0 |
| Behenyl Alcohol (C22) | 8.63 | I0 |
| Benzene (2.28) | 9.08 | E |
| PEG-20 Stearate | 9.08 | J3 |
| Ceteth-20 | 9.10 | H |
| Methyl Butyl Methacrylate CO | 8.10 | M |
| Octyl Methoxycinnamate | 9.10 | M |
| Methyl Butyl Ketone | 9.11 | E |
| Myristyl Alcohol (C14) | 9.16 | IO |
| Polysorbate-20 | 9.16 | J3 |
| THF (7.58) | 9.16 | E |
| BHT | 9.17 | D |
| Tocopherol | 9.17 | M |
| Lauryl Lactate | 9.18 | M |
| PEG-40 Stearate | 9.18 | J3 |
| Ethyl Acetate (6.02) | 9.19 | CO |
| Tributyl Citrate | 9.20 | M |
| Ethyl Acrylate | 9.22 | A |
| Propionaldehyde | 9.22 | A |
| Methyl Propyl Ketone | 9.27 | C |
| Dipropyl Nitrosamine | 9.29 | B |
| alpha-Bisabolol | 9.30 | M |
| *Pseudomonas Aeroginosa* | 9.30 | P |
| *Trichomonas Ment.* | 9.30 | P |
| Caprylic Acid (C8) (2.45) | 9.32 | E0 |
| Cetyl Lactate | 9.32 | M |
| PEG-100 Stearate | 9.35 | J3 |
| Trimethyl Citrate | 9.39 | H |
| *Klebsiella Pneumoniae* | 9.40 | P |
| Methyl Methacrylate Copolymer | 9.40 | H |
| Nicotine | 9.40 | C |
| Camphor | 9.45 | C |
| Oxidized Polyethylene (AC392) | 9.50 | * 0 |
| Lauryl Alcohol (C12) | 9.51 | C0 |
| Pulegone | 9.51 | A |
| Cholesterol | 9.55 | 0 |
| Carbon Tetrachloride (2.23) | 8.64 | C |
| Butyl Mercaptan | 8.65 | KA |
| Isostearyl Alcohol | 8.67 | 0 |
| Lauraldehyde | 8.68 | A |
| Ethyl Caproate (C6) | 8.69 | A |
| Cholesteryl Propionate | 8.70 | * |
| Isocetyl Alcohol | 8.71 | M |
| Bornyl Acetate | 8.74 | CA |
| Ethyl Mercaptan | 8.75 | K |
| Decanone-2 | 8.76 | A |
| Octanal | 8.77 | C |
| Trifluoroactylacetone | 8.77 | A |
| Cholesteryl Myristate | 8.80 | * |
| Zinc Stearate | 8.80 | 0 |
| *Citronella* | 8.83 | C0 |
| Diethyl Ketone (17.00) | 8.85 | E |
| Methyl Isobutyl Ketone (14.70) | 8.85 | E0 |
| Oxidized Polyethylene (AC629) | 8.85 | * 0 |
| Methyl Heptyl Ketone | 8.86 | A |
| Myristyl Lactate | 8.87 | M |
| Capric Acid (C10) | 8.88 | I0 |
| Methyl Caproate (CB) | 8.88 | B |
| Arachidyl Alcohol (C20) | 8.89 | CO |
| Dipropyl Ketone | 8.89 | C |
| Muscone | 8.89 | CO |
| *Candida Albicans* | 8.90 | P |
| Castor Oil | 8.90 | H |
| Elaidyl Alcohol | 8.90 | CO |
| beta-Ionone | 8.90 | CO |
| Polystyrene | 8.90 | M |
| Nicoteine | 10.08 | C |
| Octanol/Caprylic (C8) Alcohol (10.34) | 10.09 | CO |
| Acetic Anhydride (22.40) | 10.12 | C |
| Ethylene/Vinyl Acetate (AC430) | 9.55 | *0 |
| Methylene Chloride (9.08) | 9.55 | E |
| Dimethyl Isosorbide | 9.58 | M |
| PPG-2 Methyl Ether | 9.60 | * |
| Acetaldehyde (21.8) | 9.61 | A |
| Undecyl Alcohol | 9.51 | C0 |
| Linalool | 9.62 | C |
| Methyl Ethyl Ketone (18 50) 9 53A | 9.63 | C0 |
| Acetylacetone | 9.68 | * |
| Amyl Dimethyl PABA | 9.72 | M |
| Methyl Iodide | 9.75 | C |
| Decyl Alcohol (C10) (8.10) | 9.78 | C0 |
| Chlorine | 9.80 | * H |
| Ethylhexanol | 9.80 | A |
| Stratum Corneum-Porcine | 9.80 | * |
| Acetone (20.70) | 9.87 | C |
| Citronellol | 9.88 | A |
| Dibutyl Phthalate (6.44) | 9.88 | M |
| Menthyl Anthranilate | 9.89 | M |
| PPG-4 | 9.89 | M |
| Ethoxyethanol (29.60) | 9.90 | * M |
| Ethylene Oxide (13.90) | 9.93 | A |
| Menthol | 9.94 | C0 |
| Tributyrin | 9.97 | 0 |
| ButoxydiglycolBuCarbitol | 9.98 | * |
| Nitrous Oxide (1.60) | 10.00 | * H |
| Dioxane(2.21) | 10.01 | * |
| Ethyl Benzoate (6.02) | 10.01 | C |
| Caproic Acid (C8) (2.53) | 10.05 | E0 |
| Salicylic Acid | 10.06 | C |
| Copper Acetylacetonide | 11.60 | * |
| Sulfamethoxazole | 11.60 | J1 |
| Nerol | 10.13 | C |
| Ethyl Cinnamate | 10.14 | A |
| Diethyl Nitrosamine | 10.16 | C |
| Octyl Salicylate | 10.17 | M |
| Griseofulvin | 10.20 | M |
| Dioctyl Malate | 10.21 | M |
| Geraniol | 10.21 | CO |
| Butyl Lactate | 10.27 | AO |
| t-Butyl Alcohol (10.90) | 10.28 | CO |
| Morpholine (7.33) | 10.28 | C |
| Homosalate | 10.29 | GM |
| Valeric Acid (C5) | 10.29 | A |
| Polyethylene Terephthalate (PET) | 10.30 | * |
| Pyridine (12.3) | 10.30 | A |
| Phenyl Acetate (5.23) | 10.33 | E |
| Thiolacetic Acid | 10.38 | A |
| Methoxypropanol | 10.40 | * |
| Diethyl Toluamide | 10.46 | M |
| Nonoxynol-1 | 10.47 | * |
| Borneol | 10.48 | C |
| Methyl Benzoate (6.59) | 10.48 | E |
| Hexyl Alcohol (13.30) | 10.50 | I0 |
| SAN (85/15) | 10.50 | * |
| Butoxyethanol (9.30) | 10.53 | E |
| Formaldehyde | 10.54 | C |
| o-Nitrotoluene (27.40) | 10.55 | B |
| Butylparaben | 10.57 | * |
| Propionitrile | 10.57 | A |

TABLE 1-continued

Solubility of Various Chemical Components.
(from Cosmetics & Toiletries, Vol. 103, October 1988, pages 47-69)

| MATERIAL NAME (CTFA) with Dielectric Constant | Solubility Parameter (cal/cm³)^0.5 | Ref. |
|---|---|---|
| Tripropylene Glycol (PPG-3) | 10.60 | M |
| Methyl Salicylate (9.41) | 10.62 | C0 |
| Acetophenone (17.39) | 10.64 | C |
| Diacetone Alcohol (18.20) | 10.67 | CO |
| Ethyl Anthranilate | 10.67 | C |
| Naphthylene | 10.74 | B |
| PEG-4 (20.44) | 11.61 | DO |
| Acetohexamide | 11.64 | * |
| N-Methylpyrrolidone | 11.71 | A |
| Propyl Alcohol (20.10) | 11.73 | CO |
| Dimethyl Nitrosamine | 11.74 | C |
| Pentobarbital | 11.75 | J1 |
| Butadiene Diepoxide | 11.78 | A |
| Dipropylene Glycol (PPG-2) | 11.78 | M |
| Phthalide | 11.78 | C |
| Lysine | 11.79 | J1 |
| Phenethyl Alcohol | 11.79 | CO |
| Acetonitrile (375) | 11.81 | AO |
| Cinnamic Acid | 11.83 | C |
| ρ-Nitrotoluene (24.20) | 11.83 | |
| Phenoxyethanol | 11.87 | CO |
| Butobarbital | 11.90 | J1 |
| Sulfadiazine | 11.90 | * |
| Butalbital | 11.95 | J1 |
| Cinnamyl Alcohol | 11.96 | C |
| Sorbic Acid | 11.97 | MO |
| Methylparaben | 11.98 | 0 |
| Hydroxyanisole | 12.00 | C |
| Benzocaine | 12.05 | * |
| Triethylene Glycol (23.69) | 12.21 | MO |
| Alanine | 12.23 | J1 |
| Nitromethane | 12.27 | C |
| Benzyl Alcohol (I3.10) | 12.31 | 0 |
| Hexylene Glycol | 12.32 | * |
| Butyramide | 12.33 | A |
| Human Serum Albumin A | 12.33 | J1 |
| Vanillin | 12.34 | D |
| BHA | 12.37 | 0 |
| Acetic Acid (6.15) | 12.40 | CO |
| Cyclobarbital | 12.40 | J1 |
| Phenylpentanol | 10.74 | A |
| Butyric Acid (2.97) | 10.75 | E |
| Cyclopentanone | 10.77 | E |
| Thymol | 10.77 | C |
| Triacetin | 10.77 | 0 |
| Methoxyethanol (16.90) | 10.80 | * |
| Amyl Alcohol (13.90) | 10.84 | CE |
| Ethanedithiol | 10.87 | A |
| Ethyl Hexanediol | 10.89 | A |
| Trichloroacetic Acid | 10.89 | E |
| Benzalphthalide | 10.90 | 0 * |
| Testosterone | 10.90 | * |
| Cinnamaldehyde | 10.92 | C |
| Propylparaben | 10.94 | GM |
| Valine | 10.94 | J1 |
| Tolbutamide | 10.98 | * |
| Benzaldehyde (17.80) | 11.00 | CO |
| Triisopropanolamine | 11.02 | M |
| Phenylbutanol | 11.04 | A |
| Eugenol | 11.12 | C |
| D&C Red 22 (Eosin) | 11.15 | L2 |
| Butyl Alcohol (17.51) | 11.18 | C0 |
| Cellulose Acetate | 11.20 | H |
| Methyl Anthranilate | 11.22 | C |
| Caproamide (C6) | 11.24 | M |
| Isopropyl Alcohol (18.30) | 11.24 | C0 |
| Nitrocellulose | 11.25 | M0 |
| Hexobarbital | 11.30 | J1 |
| Secobarbital | 11.30 | J1 |
| ρ-Anisaldehyde | 11.32 | A |
| PEG-8 | 11.34 | MO |
| Panthenol | 11.39 | MO |
| Propionic Acid (3.35) | 11.40 | EA |
| Glyoxal | 11.46 | C |
| Diisopropanolamine | 12.40 | A |
| Ethyl Dihydroxypropyl PABA | 12.42 | M |
| o-Propylene Diamine | 12.43 | D |
| ρ-Dinitrobenzene | 12.49 | B |
| Ethyl Alcohol (24.30) | 12.55 | CO |
| Rat Gut Membrane | 12.60 | * |
| Sulfamethazine | 12.60 | J1 |
| Sulfisomidine | 12.70 | J1 |
| Sulfur (3.55) | 12.70 | * N |
| Phenol (9.78) | 12.79 | CE |
| Sulfisomidine | 12.80 | * |
| Allobarbital | 12.85 | J1 |
| o-Nitroaniline (34.50) | 12.88 | D |
| Pyruvic Acid | 12.94 | * |
| Phenobarbital | 13.00 | J1 |
| Isopropanolamine | 13.02 | A |
| Adipic Acid | 13.04 | 0 |
| BAL (2,3-Dimercapto-1-propanol) | 13.10 | B |
| Sulfathiazole | 13.10 | * |
| Aminoethyl Ethanolamine | 13.18 | M |
| Glutathione | 13.18 | G |
| Butylene Glycol | 13.20 | CO |
| m-Nitroaniline | 13.23 | C |
| Triethanolamine (29.36) | 13.28 | MO |
| Propylene Carbonate (65.00) | 13.35 | * |
| Benzamide | 13.38 | B |
| Dimethyl Sulfoxide (46.68) | 13.40 | H |
| Sulfamerazine | 13.40 | 31 |
| Propionamide | 13.46 | AC |
| Barbital | 13.50 | J1 |
| Mercaptoethanol | 13.55 | A |
| Propiolactone | 13.56 | A |
| Diethylene Glycol (31.70) | 13.61 | E0 |
| Propargyl Alcohol | 13.61 | A |
| Phenylpropanol | 11.46 | A |
| Methyl Lactate | 11.47 | CO |
| PEG-6 (16.00) | 11.47 | D0 |
| Benzoic Acid (Chameleonic) | 11.50 | * |
| PEG-5 (18.16) | 11.54 | D0 |
| Phenylalanine | 11.57 | G |
| Propylene Glycol (32.00) | 14.00 | CO |
| Theophyllin | 14.00 | * |
| Aspartic Acid | 14.11 | J1 |
| Pyrrolidinone-2 | 14.22 | |
| Ethylene Glycol (37.00) | 14.50 | CO |
| Hydroquinone | 14.62 | |
| Lactic Acid (22.00) | 14.81 | |
| Resorcinol | 14.96 | C |
| Histidine | 15.25 | J1 |
| Ethanolamine (37.72) | 15.41 | * M |
| Sodium Capryl Sulfate (14.84) | 15.80 | * |
| Erythritol | 16.06 | * |
| Formamide (109.0) | 17.82 | E |
| Lactose | 19.50 | * |
| ρ-Nitroaniline (56.30) | 13.67 | A |
| Caffeine | 13.80 | * |
| Thiodiglycol | 13.80 | M |
| Thioglycolic Acid | 13.86 | A |
| Sulfameter | 13.90 | J1 |
| Diethanolamine | 13.95 | M |
| Pyrrolidone | 14.00 | * |
| Hexyl Resorcinol | 14.06 | * |
| Sodium Lauryl Sulfate | 14.18 | * |
| Methyl Alcohol (32.70) | 14.33 | CO |
| Urea | 14.50 | G |
| Formic Acid (58.5) | 14.72 | E |
| PABA 14.56G | 14.82 | DO |
| Acetamide MEA | 15.11 | M |
| ρ-Hydroxybenzoic Acid | 15.30 | * |
| Pyrogallol | 15.41 | A |
| Acetamide (59.00) | 16.03 | C |
| Glycerin (42.50) | 16.26 | E0 |

TABLE 1-continued

Solubility of Various Chemical Components.
(from Cosmetics & Toiletries, Vol. 103, October 1988, pages 47-69)

| MATERIAL NAME (CTFA) with Dielectric Constant | Solubility Parameter $(cal/cm^3)^{0.5}$ | Ref. |
|---|---|---|
| Ammonia (16.90) | 18.08 | O |
| Water (80.10) | 23.40 | CN |

References.
NOTE:
* = Solubility Parameter value from literature
SOURCE of Physical Data
A. Aldrich Chemical Col, Catalog 1986 gram
B. Beilstein's Index
C. Chemical Rubber Handbook of Chemi. &Physics, $42^{nd}$ Ed. (1961-1962)
D. Dictionary of Organic Compounds
E. Eastman Organic Chemical Bulletin 47, No. 1, 1975
F. Fisher Scientific Catalog - 1096
G. Group Contribution Method of Hay, Van Krevelen and Feodors.
H. HANDBOOK OF SOLUBILITY PARAMETERS, A. F. Barton, Chemical Rubber Pub 1.1985
I. INDUSTRIAL WAXES, H. Bennett, Chemical Pub. Co.

In the stick compositions according to the invention, the (average) solubility parameter of the totality of the oils present in the presence of linear saturated fatty alcohols having a chain length of at least 8 carbon atoms deviates by at most $-0.7$ $(cal/cm^3)^{0.5}$ or at most $+0.7$ $(cal/cm^3)^{0.5}$, preferably by at most $-0.6$ $(cal/cm^3)^{0.5}$ or at most $+0.6$ $(cal/cm^3)^{0.5}$, particularly preferably by at most $-0.4$ $(cal/cm^3)^{0.5}$ or at most $+0.5$ $(cal/cm^3)^{0.5}$, and in the presence of water-in-oil emulsifiers which differ from linear saturated fatty alcohols having a chain length of at least 8 carbon atoms, linear saturated fatty alcohols with a chain length of at least 8 carbon atoms being absent, by at most $-0.4$ $(cal/cm^3)^{0.5}$ or at most $+0.7$ $(cal/cm^3)^{0.5}$ preferably by at most $-0.3$ $(cal/cm^3)^{0.5}$ or at most $+0.6$ $(cal/cm^3)^{0.5}$, particularly preferably by at most $-0.2$ $(cal/cm^3)^{0.5}$ or at most $+0.5$ $(cal/cm^3)^{0.5}$ from the (average) solubility parameter of the water-in-oil emulsifier/water-in-oil emulsifiers. If water-in-oil emulsifier mixtures or oil mixtures are used, the average solubility parameter of the mixture is considered in each case, specifically the arithmetic mean according to the weight fractions of the individual components. Within the scope of the invention, it is also possible for a fraction of up to 20% by weight of the constituent oils that are in a liquid state at 20° C. to consist of oils whose solubility parameter deviates by more than $-0.4$ or $-0.7$ $(cal/cm^3)^{0.5}$ or by more than $+0.7$ $(cal/cm^3)^{0.5}$, respectively, from the (average) solubility parameter of the water-in-oil emulsifier (mixture). In a particularly preferred embodiment of the invention, no oils that are in a liquid state at 20° C. are present whose solubility parameter deviates by more than $\pm 1.0$ $(cal/cm^3)^{0.5}$, preferably by $\pm 0.7$ $(cal/cm^3)^{0.5}$ and particularly preferably by $\pm 0.5$ $(cal/cm^3)^{0.5}$ from the (average) solubility parameter of the water-in-oil emulsifier/water-in-oil emulsifiers.

Lipid or Wax Matrix

The lipid or wax matrix of the stick compositions according to the invention comprises at least one lipid or wax component with a melting point of >50° C., which is not included in the nonionic oil-in-water emulsifiers with an HLB value of more than 7 or the nonionic water-in-oil emulsifiers with an HLB value greater than 1.0 and less than or equal to 7.0.

Generally, waxes are of solid to brittle consistency, coarse to finely crystalline, transparent to opaque, but not vitreous, and melt above 50° C. without decomposition. Just a little above the melting point they are of low viscosity and exhibit a heavily temperature-dependent consistency and solubility.

According to the invention, preference is given, for example, to natural vegetable waxes, e.g., candelilla wax, carnauba wax, Japan wax, sugar cane wax, ouricoury wax, cork wax, sunflower wax, fruit waxes, such as orange waxes, lemon waxes, grapefruit wax, and animal waxes, e.g., beeswax, shellac wax and spermaceti. For the purposes of the invention, it may be particularly preferred to use hydrogenated or hardened waxes. Chemically modified waxes, in particular the hard waxes, such as, for example, montan ester waxes, hydrogenated jojoba waxes and sasol waxes, can also be used as the wax component. Synthetic waxes, which are likewise preferred according to the invention, include, for example, polyalkylene waxes and polyethylene glycol waxes, $C_{20}$-$C_{40}$-dialkyl esters of dimer acids, $C_{30}$-$C_{50}$-alkyl beeswax and alkyl and alkylaryl esters of dimer fatty acids.

A particularly preferred wax component is chosen from among at least one ester of a saturated monohydric $C_{16}$-$C_{60}$-alcohol and a saturated $C_8$-$C_{36}$-monocarboxylic acid. According to the invention these also include lactides, the cyclic double esters of α-hydroxycarboxylic acids of the corresponding chain length. Esters of fatty acids and long-chain alcohols have proven particularly advantageous for the composition according to the invention because they impart excellent sensory properties to the antiperspirant preparation and high stability to the stick overall. The esters are composed of saturated, branched or unbranched monocarboxylic acids and saturated, branched or unbranched monohydric alcohols. According to the invention, it is also possible to use esters of aromatic carboxylic acids or hydroxycarboxylic acids (e.g. -12hydroxystearic acid) and saturated, branched or unbranched alcohols if the wax component has a melting point of >50° C. It is particularly preferred to choose the wax components from the group of esters of saturated, branched or unbranched alkanecarboxylic acids with a chain length from 12 to 24 carbon atoms and the saturated, branched or unbranched alcohols with a chain length from 16 to 50 carbon atoms which have a melting point of >50° C.

In particular, $C_{16-36}$-alkyl stearates and $C_{18-38}$-alkyl hydroxystearoylstearates, $C_{20-40}$-alkyl erucates and cetearyl behenate may be advantageous as the wax component. The wax or the wax components have a melting point of >50° C., preferably >60° C.

A particularly preferred embodiment of the invention comprises a $C_{20}$-$C_{40}$-alkyl stearate as wax component. This ester is known under the name Kesterwachs® K82H or Kesterwachs® K80H and is sold by Koster Keunen, Inc. It is the synthetic imitation of the monoester fraction of beeswax and is characterized by its hardness, its oil gelability and its broad compatibility with lipid components. This wax can be used as a stabilizer and as a consistency regulator for W/O and O/W emulsions. Kesterwachs offers the advantage that, even in low concentrations, it has excellent oil gelability and thus does not make the stick mass too heavy and allows for a velvety release. A further particularly preferred embodiment of the invention comprises cetearyl behenate, i.e., mixtures of cetyl behenate and stearyl behenate, as the wax component. This ester is known under the name Kesterwachs® K62 and is sold by Koster Keunen, Inc.

Further preferred lipid or wax components with a melting point of >50° C. are the triglycerides of saturated and optionally hydroxylated $C_{12-30}$ fatty acids, such as hardened triglyceride fats (hydrogenated palm oil, hydrogenated coconut oil, hydrogenated castor oil), glyceryl tribehenate (tribehenin) or glyceryl tri-12-hydroxystearate, also synthetic complete esters of fatty acids and glycols or polyols having 2-6 carbon atoms so long as they have a melting point above 50° C., for example, preferably $C_{18}$-$C_{36}$ acid triglyceride (Syncrowax® HGL-C).

According to the invention, hydrogenated castor oil, obtainable, e.g., as the commercial product Cutina® HR, is particularly preferred as the wax component.

Further preferred lipid or wax components with a melting point of >50° C. are the saturated linear $C_{14}$-$C_{36}$-carboxylic acids, in particular myristic acid, palmitic acid, stearic acid and behenic acid, and mixtures of these compounds, e.g., Syncrowax® AW 1C($C_{18}$-$C_{36}$ fatty acids) or Cutina® FS 45 (palmitic and stearic acid).

Preferred deodorant or antiperspirant sticks according to the invention are characterized in that the lipid or wax component a) is chosen from among esters of a saturated, monohydric $C_{16}$-$C_{60}$-alkanol and a saturated $C_8$-$C_{36}$-monocarboxylic acid, in particular cetyl behenate, stearyl behenate and $C_{20}$-$C_{40}$-alkyl stearate, glycerol triesters of saturated linear $C_{12}$-$C_{30}$-carboxylic acids, which may be hydroxylated, candelilla wax, carnauba wax, beeswax, saturated linear $C_{14}$-$C_{36}$-carboxylic acids, and mixtures of the above-mentioned substances. Particularly preferred lipid or wax component mixtures a) are chosen from among mixtures of cetylbehenate, stearylbehenate, hardened castor oil, palmitic acid and stearic acid. Further preferred lipid or wax component mixtures a) are chosen from among mixtures of $C_{20}$-$C_{40}$-alkyl stearate, hardened castor oil, palmitic acid, and stearic acid.

Further preferred deodorant or antiperspirant sticks according to the invention are characterized in that the total amount of lipid or wax component(s) a) is 4-20% by weight, preferably 8-15% by weight, relative to the overall composition. In a particularly preferred embodiment, the ester/esters of a saturated, monohydric $C_{16}$-$C_{60}$-alcohol and a saturated $C_8$-$C_{36}$-monocarboxylic acid, which represent(s) the lipid or wax component(s) a), comprise(s) 2-10% by weight, preferably 2-6% by weight, relative to the overall composition.

Oil-in-Water Emulsifiers.

The stick compositions according to the invention comprise at least one nonionic oil-in-water emulsifier with an HLB value of more than 7. These are emulsifiers generally known to the person skilled in the art, as listed, for example, in Kirk-Othmer, "Encyclopedia of Chemical Technology," 3rd edition, 1979, volume 8, pages 913-916. For ethoxylated products, the HLB value is calculated according to the formula HLB=(100-L):5, where L is the weight fraction of the lipophilic groups, i.e., of the fatty alkyl or fatty acyl groups, in the ethylene oxide adducts, expressed in percent by weight.

In selecting nonionic oil-in-water emulsifiers that are suitable according to the invention, it is particularly preferred to use a mixture of nonionic oil-in-water emulsifiers in order to be able to optimally adjust the stability of the stick compositions according to the invention. Here, the individual emulsifier components contribute to the overall HLB value or average HLB value of the oil-in-water emulsifier mixture according to their quantitative proportion of the total amount of the oil-in-water emulsifiers. According to the invention, the average HLB value of the oil-in-water emulsifier mixture is 10-19, preferably 12-18 and particularly preferably 14-17. In order to achieve such average HLB values, oil-in-water emulsifiers from the HLB value ranges 10-14, 14-16 and optionally 16-19 are preferably combined with one another. The oil-in-water emulsifier mixtures can, of course, also comprise nonionic emulsifiers with HLB values in the range from >7-10 and 19-20; such emulsifier mixtures may likewise be preferred according to the invention. However, in another preferred embodiment, the deodorant or antiperspirant sticks according to the invention can also comprise just one oil-in-water emulsifier with an HLB value in the range of 10-19.

Preferred deodorant or antiperspirant sticks according to the invention are characterized in that the nonionic oil-in-water emulsifiers b) are chosen from among ethoxylated $C_8$-$C_{24}$-alkanols with, on average, 10-100 mol ethylene oxide per mole, ethoxylated $C_8$-$C_{24}$-carboxylic acids with, on average, 10-100 mol ethylene oxide per mole, silicone copolyols with ethylene oxide units or with ethylene oxide and propylene oxide units, alkyl mono- and oligoglycosides having 8 to 22 carbon atoms in the alkyl moiety, and ethoxylated analogs thereof, ethoxylated sterols, partial esters of polyglycerols with 2 to 10 glycerol units and esterified with 1 to 4 saturated or unsaturated, linear or branched, optionally hydroxylated $C_8$-$C_{30}$-fatty acid moieties, provided they have an HLB value of more than 7, and mixtures of the above-mentioned substances.

The ethoxylated $C_{8-24}$-alkanols have the formula $R^{10}(CH_2CH_2O)_nH$, where $R^1$ is a linear or branched alkyl and/or alkenyl group having 8-24 carbon atoms and n, the average number of ethylene oxide units per molecule, denotes 10-100, preferably 10-30 mol ethylene oxide per 1 mol caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical-grade mixtures thereof. Adducts of 10-100 mol ethylene oxide onto technical-grade fatty alcohols having 12-18 carbon atoms, such as, for example, coconut, palm, palm kernel or tallow fatty alcohol, are also suitable.

The ethoxylated $C_8$-$C_{24}$-carboxylic acids have the formula $R^1(OCH_2CH_2)_nOH$ where $R^1$ is a linear or branched saturated or unsaturated acyl group having 8-24 carbon atoms and n, the average number of ethylene oxide units per molecule, denotes 10-100 mol, preferably 10-30 mol, ethylene oxide per 1 mol caprylic acid, 2-ethylhexanoic acid, capric acid, lauric acid, isotridecanoic acid, myristic acid, cetyl acid, palmitoleic acid, stearic acid, isostearic acid, oleic acid, elaidic acid, petroselic acid, arachidic acid, gadoleic acid, behenic acid, erucic acid and brassidic acid, and technical-grade mixtures thereof. Adducts of 10-100 mol of ethylene oxide onto technical-grade fatty acids having 12-18 carbon atoms, such as coconut, palm, palm kernel or tallow fatty acids, are also suitable. Particular preference is given to PEG-50 monostearate, PEG-100 monostearate, PEG-50 monooleate, PEG-100 monooleate, PEG-50 monolaurate and PEG-100 monolaurate.

Particular preference is given to using the $C_{12}$-$C_{18}$-alkanols or the $C_{12}$-$C_{18}$ carboxylic acids having in each case 10-30 units of ethylene oxide per molecule, and mixtures of these substances, in particular Ceteth-12, Ceteth-20, Ceteth-30, Steareth-12, Steareth-20, Steareth-30, Laureth-12 and Beheneth-20.

In addition, $C_8$-$C_{22}$-alkyl mono- and oligoglycosides are preferably used. $C_8$-$C_{22}$-alkyl mono- and oligoglycosides constitute known standard commercial surfactants and emulsifiers. They are prepared, in particular, by reacting glucose or oligosaccharides with primary alcohols having 8-22 carbon atoms. With regard to the glycoside group, both monoglycosides in which a cyclic sugar group is bonded glycosidically to the fatty alcohol, and also oligomeric glycosides with a degree of oligomerization up to about 8, but preferably of 1-2, are suitable. The degree of oligomerization here is a statistical average value which is based on a homologous distribution such as is customary for such technical products. Products which are obtainable under the trademark Plantacare® comprise a glucosidically bonded $C_8$-$C_{16}$-alkyl group on an-aligoglucoside group whose average degree of oligomerization is 12, preferably 1.2-1.4. Particularly preferred $C_8$-$C_{22}$-alkyl mono- and oligoglycosides are chosen from among octyl glucoside, decyl glucoside, lauryl glucoside, palmityl glucoside, isostearyl glucoside, stearyl glucoside, arachidyl glucoside and behenyl glucoside, and mixtures thereof. The acylglucamides derived from glucamine are also suitable as nonionic oil-in-water emulsifiers.

Ethoxylated sterols, in particular, ethoxylated soya sterols, also represent suitable oil-in-water emulsifiers according to the invention. The degree of ethoxylation must be greater than 5, but preferably at least 10, in order to have an HLB value greater than 7. Suitable commercial products are, e.g., PEG-10 Soy Sterol, PEG-16 Soy Sterol and PEG-25 Soy Sterol.

In addition, partial esters of polyglycerols having 2 to 10 glycerol units and esterified with 1 to 4 saturated or unsaturated, linear or branched, optionally hydroxylated $C_8$-$C_{30}$-fatty acid groups are preferably used, provided they have an HLB value of more than 7. Particular preference is given to diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol manocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate and decaglycerol trihydroxystearate.

Particularly preferred deodorant or antiperspirant sticks according to the invention are characterized in that the amount of nonionic oil-in-water emulsifier b) relative to the overall composition is 0.5-10% by weight, particularly preferably 1-4% by weight and extremely preferably 1.5-3% by weight.

Water-in-Oil Emulsifiers.

The stick compositions according to the invention further comprise at least one nonionic water-in-oil emulsifier with an HLB value greater than 1.0 and less than or equal to 7.0 as a consistency regulator and/or water binder, which is chosen from among the mono- and diesters of ethylene glycol and the mono- and di-, tri- and tetraesters of pentaerythritol having linear saturated fatty acids having 12-30, but especially 14-22, carbon atoms that can be hydroxylated, as well as mixtures thereof. The mono- and diesters are particularly preferred. The $C_{12}$-$C_{30}$-fatty acid groups that are preferred according to the invention are chosen from among lauric acid, myristic acid, palmitic acid, stearic acid, arachidic acid, and behenic acid groups; the stearic acid group is particularly preferred. The nonionic water-in-oil emulsifiers with an HLB value of greater than 1.0 and less than or equal to 7.0 that are particularly preferred according to the invention are chosen from among pentaerythrityl monostearate, pentaerythrityl distearate, pentaerythrityl tristearate, pentaerythrityl tetrastearate, ethylene glycol monostearate, ethyleneglycol distearate, and mixtures thereof. The water-in-oil emulsifier(s) mainly contribute(s) to the structure of the lipophilic gel phase which surrounds the dispersed lipid/wax/oil phase, as well as, albeit to a lesser extent, to the structure of the hydrophilic gel phase which stabilizes the aqueous phase. Suitable water-in-oil emulsifiers with an HLB value greater than 1.0 and less than or equal to 7.0 according to the invention are commercially available under the brand name Cutina PES (INCI: pentaerythrityl distearate), Cutina AGS (INCI: Glycol distearate), or Cutina EGMS (INCI: glycol stearate). These products are already mixtures of mono- and diesters (tri- and tetraesters are also contained in the pentaerythrityl esters). According to the invention it may be advantageous to use only a single water-in-oil emulsifier. In another advantageous embodiment, the compositions of the invention contain mixtures, especially technical-grade mixtures, of at least two water-in-oil emulsifiers. A technical-grade mixture is a mixture such as, for example, Cutina® PES.

Besides the cited water-in-oil emulsifiers on a base of ethylene glycol ester or pentaerythrityl ester, in a preferred embodiment at least one additional nonionic water-in-oil emulsifier with an HLB value greater than 1.0 and less than or equal to 7.0 can be included, whose amount should not exceed 80% by weight relative to the total weight of the nonionic water-in-oil emulsifiers with an HLB value greater than 1.0 and less than or equal to 7.0. In a particularly preferred embodiment, the amount of the at least one additionally included nonionic water-in-oil emulsifier with an HLB value greater than 1.0 and less than or equal to 7.0 is at most 10% by weight, or optionally no such additional emulsifiers are included. Some of these emulsifiers are listed, for example, in Kirk-Othmer, "Encyclopedia of Chemical Technology," 3rd edition, 1979, volume 8, page 913. For ethoxylated adducts, the HLB value, as already mentioned, can also be calculated.

Preferred water-in-oil emulsifiers are:
linear saturated alkanols having 12-30 carbon atoms, in particular, having 16-22 carbon atoms, in particular, cetyl alcohol, stearyl alcohol, arachidyl alcohol, behenyl alcohol and lanolin alcohol or mixtures of these alcohols, as are obtainable in the industrial hydrogenation of vegetable and animal fatty acids;
esters and, in particular, partial esters of a polyol having 3-6 carbon atoms (except pentaerythritol) and linear saturated and unsaturated fatty acids having 12-30, in particular 14-22, carbon atoms, which may be hydroxylated. Such esters or partial esters are, for example, the monoesters and diesters of glycerol or the monoesters of propylene glycol with linear saturated and unsaturated $C_{12}$-$C_{30}$-carboxylic acids, which may be hydroxylated, in particular those with palmitic acid and stearic acid, the sorbitan mono-, di- or triesters of linear saturated and unsaturated $C_{12}$-$C_{30}$-carboxylic acids, which may be hydroxylated, in particular those of myristic acid, palmitic acid, stearic acid or of mixtures of these fatty acids, and the methylglucose mono- and diesters of linear, saturated and unsaturated $C_{12}$-$C_{30}$-carboxylic acids, which may be hydroxylated;
sterols, i.e., steroids which carry a hydroxyl group on the C3 atom of the steroid backbone and are isolated both from animal tissue (zoosterols, e.g., cholesterol, lanosterol) and also from plants (phytosterols, e.g., ergosterol, stigmasterol, sitosterol) and from fungi and yeasts (mycosterols) and which may have low degrees of ethoxylation (1-5 EO);
alkanols and carboxylic acids having in each case 8-24 carbon atoms, in particular having 16-22 carbon atoms, in the alkyl group and 1-4 ethylene oxide units per molecule, which have an HLB value greater than 1.0 and less than or equal to 7.0, glycerol monoethers of saturated and/or unsaturated, branched and/or unbranched alcohols with a chain length of 8-30, in particular 12-18, carbon atoms;

partial esters of polyglycerols having n=2 to 10 glycerol units and esterified with 1 to 5 saturated or unsaturated, linear or branched, optionally hydroxylated $C_8$-$C_{30}$-fatty acid groups, provided they have an HLB value of less than or equal to 7, and mixtures of the above-mentioned substances.

According to the invention, it may be preferred to use just one additional water-in-oil emulsifier. In another preferred embodiment, the compositions according to the invention comprise mixtures, in particular technical-grade mixtures, of at least two additional water-in-oil emulsifiers. A technical-grade mixture is understood, for example, as meaning a commercial product such as Cutina® GMS, which constitutes a mixture of glyceryl monostearate and glyceryl distearate.

Additional water-in-oil emulsifiers which can be used particularly advantageously are stearyl alcohol, cetyl alcohol, glyceryl monostearate, in particular, in the form of the commercial products Cutina® GMS and Cutina® MD (ex Cognis), glyceryl distearate, glyceryl monocaprate, glyceryl monocaprylate, glyceryl monolaurate, glyceryl monomyristate, glyceryl monopalmitate, glyceryl monohydroxystearate, glyceryl monooleate, glyceryl monolanolate, glyceryl dimyristate, glyceryl dipalmitate, glyceryl dioleate, propylene glycol monostearate, propylene glycol monolaurate, sorbitan monocaprylate, sorbitan monolaurate, sorbitan monomyristate, sorbitan monopalmitate, sorbitan monostearate, sorbitan sesquistearate, sorbitan distearate, sorbitan dioleate, sorbitan sesquioleate, sucrose distearate, arachidyl alcohol, behenyl alcohol, polyethylene glycol (2) stearyl ether (Steareth-2), Steareth-5, Oleth-2, diglycerol monostearate, diglycerol monoisostearate, diglycerol monooleate, diglycerol dihydroxystearate, diglycerol distearate, diglycerol dioleate, triglycerol distearate, tetraglycerol monostearate, tetraglycerol distearate, tetraglycerol tristearate, decaglycerol pentastearate, decaglycerol pentahydroxystearate, decaglycerol pentaisostearate, decaglycerol pentaoleate, soy sterol, PEG-1 soy sterol, PEG-5 soy sterol, PEG-2 monolaurate and PEG-2 monostearate.

Preferred deodorant or antiperspirant sticks according to the invention are characterized in that, in addition to the nonionic water-in-oil emulsifier c), they contain at least one additional nonionic water-in-oil emulsifier, which is chosen from among the following substances:

linear saturated $C_{12}$-$C_{30}$-alkanols, glycerol mono- and diesters of linear, saturated and unsaturated $C_{12}$-$C_{30}$-carboxylic acids, which may be hydroxylated, propylene glycol mono- and diesters of linear, saturated and unsaturated $C_{12}$-$C_{30}$-carboxylic acids, which may be hydroxylated, sorbitan mono-, di- and triesters of linear, saturated and unsaturated $C_{12}$-$C_{30}$-carboxylic acids, which may be hydroxylated, methylglucose mono- and diesters of linear, saturated and unsaturated $C_{12}$-$C_{30}$-carboxylic acids, which may be hydroxylated, sterols, alkanols and carboxylic acids having in each case 8-24, but especially 16-22, carbon atoms in the alkyl group and 1-4 ethylene oxide units per molecule, which have an HLB value of greater than 1.0 and less than or equal to 7.0, glycerol monoethers of saturated and/or unsaturated, branched and/or unbranched alcohols with a chain length of 8-30, but especially 12-18, carbon atoms, partial esters of polyglycerols having n=2 to 10 glycerol units and esterified with 1 to 5 saturated or unsaturated, linear or branched, optionally hydroxylated $C_8$-$C_{30}$ fatty acid groups, provided they have an HLB value of less than or equal to 7, and mixtures of the above-mentioned substances.

Particularly preferred deodorant or antiperspirant sticks according to the invention are characterized in that the total amount of the nonionic water-in-oil emulsifier c) and, if provided, the optional additional nonionic water-in-oil emulsifiers named above relative to the overall composition is 0.1-15% by weight, particularly preferably 0.5-8% by weight and most preferably 1-4% by weight. In addition, amounts of from 2-3% by weight, based on the total weight of the composition, may also be most preferred according to the invention.

The following table contains various oil-in-water emulsifiers and water-in-oil emulsifiers and their HLB values. The HLB values, however, can also be calculated using Griffin's method, as, for example, in the ROMPP Chemie Lexikon, specifically the online version of November 2003, and the handbooks from Fiedler, Kirk-Othmer, and Janistyn cited there under the keyword "HLB System." As long as there is conflicting HLB data for a substance found in the literature, the HLB value that comes closest to Griffin's HLB value should be used for the teaching of the invention. If no clear HLB value can be determined this way, the HLB value stated by the manufacturer of the emulsifier should be used for the teaching of the invention. If that is not possible either, then the HLB is determined experimentally.

HLB Value Chemical Designation.

(from H. Janistyn, Handbuch der Kosmetika and Riechstoffe, Hüthig-Verlag Heidelberg, 3. edition, 1978, Volume 1, page 470 and Volume 3, pages 68-78))

1 Triglycerides of saturated fatty acids
   Glyceryltrioleate
1.5 Ethyleneglycol distearate
1.6 Pure cellin oil
1.8 Sorbitan trioleate
   Glycerol dioleate
2.1 Sorbitan tristearate
2.4 Propylene glycol lactostearate
2.7 Glycerol monooleate
   Sorbitol dioleate
2.8 Glycerol monostearate
   Propylene glycol mono-/distearate, non-self-emulsifying
3.0 Decaglycerol decaoleate
   Decaglycerol decastearate
   Generol 122 (Rapeseed Sterols)
   Sucrose distearate
3.1 Decaglycerol decaoleate
   Glyceryl monoricinoleate
   Pentaerythrityl monostearate
   Pentaerythrityl sesquioleate
3.2 Ethyleneglycol monodistearate, non-self-emulsifying
   Glycolstearate
3.3 Glycerol monolaurate
3.4 Propylene glycol monostearate
3.5 Ethylene glycol monostearate
   Pentaerythrityl monooleate
   Polyethylene glycol (100)monooleate 3.6 Glycerol mono-/dioleate, non-self-emulsifying
Monoethoxylauryl ether
3.7 Sorbitan sesquioleates (Dehymuls SSO)
3.8 Glycerol monodistearate, non-self-emulsifying
Polyethylene glycol (100) monostearates
Diglycerol sesquioleates
N,N-Dimethylcaproamide
Pentaerythrityl monotallowates
Propylene glycol monolaurate
4.0 Decaglycerol octaoleate
4.3 Sorbitan monooleate (Dehymuls SMO)
Diethylene glycol monostearate
4.4 1,2-Propylene glycol monodistearate, self-emulsifying
4.5 Glycerol monostearate palmitate (90%), non-self-emulsifying
Propylene glycol monolaurate
4.7 Sorbitan monostearate (Dehymuls SMS)
Diethylene glycol monooleate
4.8 Pentaerythrityl monolaurate
4.9 Polyoxyethylene(2)oleyl alcohol (Polyoxyethylene(2) oleyl ether)
Polyoxyethylene(2)stearyl alcohol (Polyoxyethylene(2) stearyl ether)
5.0 Generol 122 E 5 (PEG-5 Soy Sterol)
Polyethylene glycol (100) monoricinoleate
Polyethylene glycol (200) distearate
Polyglyceryl-3-isostearate (e.g., Isolan GI 34 by Tego)
5.9 Polyethylene glycol (200) dilaurate
6.0 Decaglycerol tetraoleate
Polyethylene glycol (100) monolaurates
Polyethylene glycol (200) dioleate
6.3 Polyethylene glycol (300) dilaurates
6.4 Glycerol monoricinoleate
Glycerol sorbitan monolaurate
6.5 Diethylene glycol monolaurate
Sodium stearoyl-2-lactylate
6.7 Sorbitan monopalmitate
6.8 Glycerol monococoate
Glycerol monolaurate
7.0 Polyoxyethylen(2)C10-C14-fatty alcohol ether, Laureth-2 (Dehydrol LS 2)
Sucrose distearate
7.2 Polyethylene glycol (400) dioleate
Sucrose dioleate
7.4 Polyethylene glycol (100) monolaurate
7.5 Sucrose dipalmitate
7.6 Glycerol sorbitan laurate
7.8 Polyethylene glycol (400) distearates
7.9 Polyethylene glycol (200) monostearate
Polyoxyethylene (3) tridecyl alcohol
8-8.2 Polyethylene glycol (400) distearate
8.0 Polyoxyethylene(3)C10-C14-fatty alcohol, Laureth-3 (Dehydrol LS 3)
N,N-Dimethyllauramide
Sodium lauroyl lactylate, sodium lauroyl-2-lactylate
Polyethylene glycol (200) monooleate
Polyethylene glycol (220) monotallowate
Polyethylene glycol (1500) dioleate
Polyoxyethylene (4) oleyl alcohol
Polyoxyethylene (4) stearylcetyl ether
8.2 Triglycerol monooleate
8.3 Diethylene glycol monolaurate
8.4 Polyoxyethylene (4) cetylether
Polyoxyethylene glycol (400) dioleate
8.5 Sodium caproyl lactylate
Polyethylene glycol (200) monostearate
Sorbitan monooleate
8.6 Sorbitan monolaurate (Dehymuls SML)
Polyethylene glycol (200) monolaurate
8.8 Polyoxyethylene (4) myristyl ether
Polyethylene glycol (400) dioleate
8.9 Nonylphenol, polyoxyethylated with 4 Mol EO
9.0 Oleth-5 (z. B. Eumulgin O 5)
9.2-9.7 Polyoxyethylene (4) lauryl alcohol (according to commercial product, e.g., Brij 30, Dehydrol LS 4)
9.3 Polyoxyethylene (4) tridecyl alcohol
9.6 Polyoxyethylene (4) sorbitan monostearate
9.8 Polyethylenglycol (200) monolaurate
10-11 Polyethylene glycol (400) monooleate
10.0 Didodecyldimethylammoniumchloride
10.0 Polyethylene glycol (200) monolaurate
Polyethylene glycol (400) dilaurate
Polyethylene glycol (600) dioleate
Polyoxyethylene (4) sorbitan monostearate
Polyoxyethylene (5) sorbitan monooleate
10.2 Polyoxyethylene (40) sorbitol hexaoleate
10.4-10.6 Polyoxyethylene glycol (600) distearate
10.5 Polyoxyethylene (20) sorbitan tristearate
10.6 Sucrose monostearate
10.7 Sucrose monooleate
11-11.4 Polyethylene glycol (400) monooleate
11.0 Polyethylene glycol (350) monostearate
Polyethylene glycol (400) monotalleate
Polyoxyethylene glycol (7) monostearate
Polyoxyethylene glycol (8) monooleate
Polyoxyethylene (20) sorbitan trioleate
Polyoxyethylene (6) tridecyl alcohol
11.1 Polyethylene glycol (400) monostearate
11.2 Polyoxyethylene (9) monostearate
Sucrose monooleate
Sucrose monostearate
11.4 Polyoxyethylene (50) sorbitol hexaoleate
Sucrose monotalleate
Sucrose stearate palmitate
11.6 Polyoxyethylene glycol (400) monoricinoleate
11.7 Sucrose monomyristeate
Sucrose monopalmitate
12.0 PEG-10 Soy Sterol (e.g., Generol 122 E 10)
Triethanolamine oleate
12.2-12.3 Nonylphenol, ethoxylated with 8 Mol EO
12.2 Sucrose monomyristeate
12.4 Sucrose monolaurate
Polyoxyethylene (10) oleyl alcohol, polyoxyethylene (10) oleyl ether
Polyoxyethylene (10) stearyl alcohol, polyoxyethylene (10) stearyl ether
12.5 Polyoxyethylene (10) stearylcetyl ether
12.7 Polyoxyethylene (8) tridecyl alcohol
12.8 Polyoxyethylene glycol (400) monolaurate
Sucrose monococoate
12.9 Polyoxyethylene (10) cetylether
13 Glycerol monostearate, ethoxylated (20 Mol EO)
13.0 Eumulgin O 10
Eumulgin 286
Eumulgin B 1 (Ceteareth-12)
13.0 C12-fat amines, ethoxylated (5 Mol EO)
13.1 Nonylphenol, ethoxylated (9.5 Mol EO)
13.2 Polyethylene glycol (600) monostearate
Polyoxyethylene (16) tallow oil
13.3 Polyoxyethylene (4) sorbitan monolaurate
13.5 Nonylphenol, ethoxylated (10.5 Mol EO)
Polyethylene glycol (600) monooleate
13.7 Polyoxyethylene (10) tridecyl alcohol Polyethylene glycol (660) monotallowate
Polyethylene glycol (1500) monostearate
Polyoxyethylene glycol (1500) dioleate
13.9 Polyethylene glycol (400) monococoate
Polyoxyethylene (9) monolaurate
14-16 Eumulgin HRE 40 (Ricinus oil, ethoxylated and hydroxylated with 40 EO)
14.0 Polyoxyethylene (12) lauryl ether
Polyoxyethylene (12) tridecyl alcohol
14.2 Polyoxyethylene (15) stearyl alcohol
14.3 Polyoxyethylene (15) stearylcetyl ether
14.4 Mixture of $C_{12}$-$C_{15}$-fatty alcohols with 12 Mol EO
14.5 Polyoxyethylene (12) lauryl alcohol
14.8 Polyoxyethylene glycol (600) monolaurate
14.9-15.2 Sorbitan monostearate, ethoxylated with 20 EO (e.g., Eumulgin SMS 20)
15-15.9 Sorbitan monooleate, ethoxylated with 20 EO (e.g., Eumulgin SMO 20)
15.0 PEG-20 Glyceryl stearate (e.g., Cutina E 24)
PEG-40 Castor Oil (e.g., Eumulgin RO 40)
Decyl glucoside (Oramix NS 10)
Dodecyl glucoside (Plantaren APG 600)
Dodecyl trimethyl ammonium chloride
Nonylphenol, ethoxyalted with 15 Mol EO
Polyethylene glycol (1000) monostearate
Polyoxyethylene (600) monooleate
15-17 Eumulgin HRE 60 (Ricinus oil, ethoxylated and hydrated with 60 EO)
15.3 C12-fat amines, polyoxyethylated with 12 Mol EO
Polyoxyethylene (20) oleyl alcohol, polyoxyethylene (20) oleylether
15.4 Polyoxyethylene (20) stearylcetylether (z. B. Eumulgin B 2 (Ceteareth-20))
15.5 Polyoxyethylene (20) stearyl alcohol
15.6 Polyoxyethylene glycol (1000)monostearate
Polyoxyethylene (20) sorbitan monopalmitate
15.7 Polyoxyethylene (20) cetyl ether
15.9 Disodium triethanolamine distearyl heptaglycol ether sulfosuccinate
16.0 Nonylphenol ethoxylated with 20 Mol EO
Polyoxyethylene (25) propylene glycol stearate
16-16.8 Polyoxyethylene (30) monostearate
16.3-16.9 Polyoxyethylene (40) monostearate
16.5-16.7 Polyoxyethylene (20) sorbitan monolaureate (e.g., Eumulgin SML 20)
16.6 Polyoxyethylene (20) sorbitol
16.7 C18 fat amines polyoxyethylated with 5 Mol EO
Polyoxyethylene (23) lauryl alcohol
17.0 Ceteareth-30. z. B. Eumulgin B 3
Octyl glucoside (Triton CG 110)
Polyoxyethylene (30) glyceryl monolaurate
17.1 Nonylphenol, ethoxylated with 30 Mol EO
17.4 Polyoxyethylene (40) stearyl alcohol Further preferred stick compounds according to the invention are those wherein the total content of nonionic and ionic emulsifiers and/or surfactants with an HLB value above 8 is a maximum of 20% by weight, a preferred maximum of 15% by weight, a particularly preferred maximum of 10% by weight, a particularly preferred maximum of 7% by weight, a further particularly preferred maximum of 4% by weight, and an exceptionally preferred maximum of 3% by weight, referring respectively to the total compound according to the invention.

Oils.

The stick compounds according to the invention contain further at least one oil, which is liquid at 20° C., which does not represent a fragrance component and no essential oil, whereby the (average) solubility parameter of the total of the contained oils in the presence of linear saturated fatty alcohols with a chain length of at least 8 carbon atoms differs by a maximum of $-0.7$ $(cal/cm^3)^{0.5}$ resp. a maximum of $+0.7$ $(cal/cm^3)^{0.5}$, preferably by a maximum of $-0.6$ $(cal/cm^3)^{0.5}$ resp. a maximum of $+0.6$ $(cal/cm^3)^{0.5}$, particularly preferably by a maximum of $-0.4$ $(cal/cm^3)^{0.5}$ resp. a maximum of $+0.5$ $(cal/cm^3)^{0.5}$, and in the presence of water-in-oil emulsifiers, which are different from linear saturated fatty alcohols with a chain length of at least 8 carbon atoms, in the absence of linear saturated fatty alcohols with a chain length of at least 8 carbon atoms by a maximum of $-0.4$ $(cal/cm^3)^{0.5}$ resp. a maximum of $+0.7$ $(cal/cm^3)^{0.5}$, preferably by a maximum of $-0.3$ $(cal/cm^3)^{0.5}$ resp. a maximum of $+0.6$ $(cal/cm^3)^{0.5}$, particularly preferably by a maximum of. $-0.2$ $(cal/cm^3)^{0.5}$ resp. a maximum of $+0.5$ $(cal/cm^3)^{0.5}$, from the (average) solubility parameter of the water-in-oil emulsifier(s). The matching of the used oil(s) with the used water-in-oil emulsifier(s) represents an important parameter of this invention. If the water-in-oil emulsifiers and the oil component(s) do not match each other in their solubility parameter within the required limits, one will get sticks with an unsatisfactory degree of hardness and stability from the point of view of usage.

Preferred oils according to the invention are chosen from branched saturated or unsaturated fatty alcohols with 6-30 carbon atoms. These alcohols are often also known as Guerbet Alcohols, as they are obtained by the Guerbet Reaction. Preferred Guerbet Alcohol oils are hexyldecanol (Eutanol® G 16, Guerbitol® T 16), octyldodecanol (Eutanol® G, Guerbitol® 20), 2-ethylhexylalcohol and the commercial products Guerbitol® 18, Isofol® 12, Isofol® 16, Isofol® 24, Isofol® 36, Isocarb® 12, Isocarb® 16 or Isocarb® 24.

Further preferred oil components are mixtures of Guerbet Alcohols and Guerbet Alcohol esters, for example, the commercial product Cetiol® PGL (hexyldecanol and hexyldecyllaurate).

Further preferred oils according to the invention are chosen from the triglycerides of linear or branched, saturated or unsaturated, optionally hydroxylated $C_{8-30}$-fatty acids. The use of natural oils e.g., Soya oil, cottonseed oil, sunflower oil, palm oil, palm seed oil, linseed oil, Almond oil, castor oil, corn oil, olive oil, rapeseed oil, sesame seed oil, safflower oil, wheat germ oil, peach seed oil and the liquid parts of coconut oil and the like can be particularly suitable. Suitable are however also synthetic triglycerides, in particular capric/caprylic triglycerides, e.g., the commercial products Myritol® 318, Myritol® 331 (Cognis) or Miglyol® 812 (Huls) with non-branched fatty acid residues as well as glyceryl tri-isostearine and the commercial products Estol® GTEH 3609 (Uniqema) or Myritol® GTEH (Cognis) with branched fatty acid residues.

Further particularly preferred oils according to the invention are chosen from the dicarboxylic acid esters of linear or branched $C_2$-$C_{10}$-alkanols, in particular di-isopropyladipate, di-n-butyladipate, di-(2-ethylhexyl)adipate, dioctyladipate, diethyl-/di-n-butyl/dioctylsebacate, diisopropylsebacate, dioctylmalate, dioctylmaleate, dicaprylylmaleate, di-isooctylsuccinate, di-2-ethylhexylsuccinate and di-(2-hexyldecyl)-succinate.

Further particularly preferred oils according to the invention are chosen from the addition products of 1 to 5 propylene oxide units to monohydric or polyhydric $C_{8-22}$-alkanols such as octanol, decanol, decanediol, lauryl alcohol, myristyl alcohol and stearyl alcohol, e.g., PPG-2-myristylether and PPG-3-myristylether (Witconol® APM).

For the use of the oils listed below in the stick compounds according to the invention, care is to be taken that their share in the total oil mixture is only so large that the average solubility parameter of the entire oil mixture, as required by the invention and described above, matches the average solubility parameter of the water-in-oil emulsifiers. Corresponding oils are chosen from the esters of the linear or branched saturated or unsaturated fatty alcohols with 2-30 carbon atoms, which can be hydroxylated. Among these are hexyldecylstearate (Eutanol® G 16 S), hexyldecyllaurate, isodecylneopentanoate, isononylisononanoate, 2-ethylhexylpalmitate (Cegesoft® C 24) and 2-ethylhexylstearate (Cetiol® 868). Similarly, limitedly suitable are isopropylmyristate, isopropylpalmitate, isopropylstearate, isopropylisostearate, isopropyloleate, iso-octylstearate, isononylstearate, isocetylstearate, isononylisononanoate, isotridecylisononanoate, cetearylisononanoate, 2-ethylhexyllaurate, 2-ethylhexylisostearate, 2-ethylhexylcocoate, 2-octyldodecyl palmitate, butyloctane acid-2-butyloctanoate, diisotri-decylacetate, n-butylstearate, n-hexyllaurate, n-decyloleate, oleyloleate, oleylerucate, erucyl-oleate, erucylerucate, ethylenglycoldioleate and -dipalmitate.

Further oils, which are, in consideration of the solubility parameter matching, usable only in small quantities or not usable at all, are chosen from the addition products of at least 6 ethylene oxide and/or propylene oxide units to monohydric or polyhydric $C_{3-22}$-alkanols such as butanol, butanediol, myristyl alcohol and stearyl alcohol, e.g., PPG-14-butylether (Ucon Fluid® AP), PPG-9-butylether (Breox® B25), PPG-10-butanediol (Macol® 57) and PPG-15-stearylether (Arlamol® E).

Further oils, which are, in consideration of the solubility parameter matching, usable only in small quantities or not usable at all, are chosen from the $C_8$-$C_{22}$-fatty alcohol esters of monovalent or polyvalent $C_2$-$C_7$-hydroxycarboxylic acids, in particular the esters of glycol acid, lactic acid, malic acid, tartaric acid, citric acid and salicylic acid. Such esters based on linear $C_{14/15}$-alkanols, e.g. $C_{12}$-$C_{15}$-alkyllactate, and of $C_{12/13}$-alkanols branched in the 2-position are to be had under the product name of Cosmacol® of the firm Nordmann, Rassmann GmbH & Co, Hamburg, in particular the commercial products Cosmacol® ESI, Cosmacol® EMI and Cosmacol® ETI.

Further oils, which are, in consideration of the solubility parameter matching, usable only in small quantities or not usable at all, are chosen from the symmetric, asymmetric or cyclic esters of the carbonic acid with fatty alcohols, e.g., glycerin carbonate, Dicaprylylcarbonate (Cetiol® CC) or the esters of the DE 197 56 454 A1.

Further oils, which are, in consideration of the solubility parameter matching, usable only in small quantities or not usable at all, are chosen from the esters of dimerized unsaturated $C_{12}$-$C_{22}$-fatty acids (dimerized fatty acids) with monohydric linear, branched or cyclic $C_2$-$C_{18}$-alkanols or with polyhydric linear or branched $C_2$-$C_6$-alkanols.

It can be preferred, according to the invention, to use mixtures of the oils named above.

Preferred deodorant or antiperspirant sticks according to the invention are those wherein in the case of oils d), liquid at 20° C., the choice is among branched saturated or unsaturated fatty alcohols with 6-30 carbon atoms, triglycerides of linear or branched, saturated or unsaturated, optionally hydroxylated $C_{8-30}$-fatty acids, dicarboxylic acid esters of linear or branched $C_2$-$C_{10}$-alkanols, esters of branched saturated or unsaturated fatty alcohols with 2-30 carbon atoms with linear or branched saturated or unsaturated fatty acids with 2-30 carbon atoms, which can be hydroxylated, addition products of 1 to 5 propylene oxide units to monohydric or polyhydric $C_{8-22}$-alkanols, addition products of at least 6 ethylene oxide and/or propylene oxide units to monohydric or polyhydric $C_{3-22}$-alkanols, $C_8$-$C_{22}$-fatty alcohol esters of monovalent or polyvalent $C_2$-$C_7$-hydroxycarboxylic acids, symmetric, asymmetric or cyclic esters of carbonic acid with fatty alcohols, the esters of dimerized unsaturated $C_{12}$-$C_{22}$-fatty acids (dimerized fatty acids) with monohydric linear, branched or cyclic $C_2$-$C_{18}$-alkanols or with polyhydric linear or branched $C_2$-$C_6$-alkanols, as well as mixtures of the substances named above.

Particularly preferred deodorant or antiperspirant sticks are those wherein the oil(s), which is/are liquid at 20° C. d) is/are contained 3-20% by weight, preferred 5-14% by weight, particularly preferred 6-12% by weight, relating respectively to the total weight of the combination, in a total quantity.

In a further particularly preferred version of the invention, the share of oil(s), whose solubility parameter differs by more than $-0.4$ resp. $-0.7$ $(cal/cm^3)^{0.5}$ or by more than $+0.7$ $(cal/cm^3)^{0.5}$ from (the average) solubility parameter of the water-in-oil emulsifier(s), is a maximum of 20% by weight in relation to the total weight of oils which are liquid at 20° C. In a further particularly preferred version of the invention no such oils are contained which are liquid at 20° C., the solubility parameter of which differs by more than $\pm 1.0$ $(cal/cm^3)^{0.5}$ from (the average) solubility parameter of the water-in-oil emulsifier(s).

Correspondingly less suitable or (depending on the water-in-oil emulsifier used), in fact, unsuitable oil components are, for example, silicon oils and hydrocarbonated oils.

Silicon oils, among which are e.g., dialkyl- and alkylarylsiloxane, such as, for example, not only cyclopentasiloxane, cyclohexasiloxane, dimethylpolysiloxane and methylphenylpolysiloxane, but also hexamethyldisiloxane, octamethyltrisiloxane and decamethyltetrasiloxane, display solubility parameters in the range of around 5.7 to 6.3 $(cal/cm^3)^{0.5}$, which is a divergence of more than 0.4 $(cal/cm^3)^{0.5}$ of the value of most of the water-in-oil emulsifiers used according to the invention.

Natural and synthetic hydrocarbons such as paraffin oils, isohexadecane, isoeicosane, polyisobutene or polydecene, which are available, for example, under the name Emery® 3004, 3006, 3010 or under the name Ethylflo® from Albemarle or Nexbase® 2004G from Nestle, as well as 1,3-Di-(2-ethylhexyl)-cyclohexane (Cetiol® S) are similarly among the less preferred oil components according to the invention.

The share of silicon oils and/or hydrocarbons in a preferred version should therefore not be more than 20% in relation to the total weight of oils which are liquid at 20° C., otherwise the sticks according to the invention do not achieve the desired hardness and stability when used. In a particularly preferred version of the invention no silicon oils and/or hydrocarbons, in particular no paraffin- and iso-paraffin hydrocarbons are contained.

Polyols.

The stick compounds according to the invention contain further at least one water soluble polyhydric $C_2$-$C_8$-alkanol with 2-6 hydroxyl groups and/or at least one water soluble polyethylene glycol with 3-20 ethylene oxide units, as well as mixtures thereof. These components are preferably chosen from 1,2-propylene glycol, 2-methyl-1,3-propanediol, glycerine, butylene glycols such as 1,2-butylene glycol, 1,3-butylene glycol and 1,4-butylene glycol, pentylene glycols such as 1,2-pentanediol and 1,5-pentanediol, hexanediols, such as 1,6-hexanediol, hexanetriols such as 1,2,6-hexanetriol, 1,2-octanediol, 1,8-octanediol, di-propylene glycol, tri-propylene glycol, di-glycerine, tri-glycerine, erythritol, sorbitol, as well as mixtures of the substances named. Suitable water soluble polyethylene glycols are chosen from PEG-3, PEG-4, PEG-6, PEG-7, PEG-8, PEG-9, PEG-10, PEG-12, PEG-14, PEG-16, PEG-18 and PEG-20, as well as mixtures thereof, whereby PEG-3 to PEG-8 are preferred. Also sugar and certain sugar derivatives such as fructose, glucose, maltose, maltitole, mannite, inosite, sucrose, trehalose and xylose are suitable according to the invention.

Preferred deodorant or antiperspirant sticks are those wherein at least one water soluble polyhydric $C_2$-$C_8$-alkanol with 2-6 hydroxyl groups and/or at least one water soluble polyethyllene glycol with 3-20 ethylene oxide units is chosen from 1,2-propylene glycol, 2-methyl-1,3-propanediol, glycerine, butylene glycol such as 1,2-butylene glycol, 1,3-butylene glycol and 1,4-butylene glycol, pentylene glycold such as 1,2-pentanediol and 1,5-pentanediol, hexanediols such as 1,6-hexanediol, hexanetriols such as 1,2,6-hexanetriol, 1,2-octanediol, 1,8-octanediol, dipropylene glycol, tripropylene glycol, diglycerine, triglycerine, erythritol, sorbitol as well as mixtures of the substances named above.

Particularly preferred deodorant or antiperspirant sticks according to the inventions contain at least one water soluble polyhydric $C_2$-$C_8$-alkanol with 2-6 hydroxyl groups and/or at least one water soluble polyethylene glycol with 3-20 ethylene oxide units in all, in quantities of 3%-30% by weight, preferably 8%-25% by weight, particularly preferred 10%-18% by weight, related respectively to the total composition.

Water.

The share of water in the composition according to the invention is 5% to less than 50% by weight, preferably 10% to less than 30% by weight, particularly preferred 15%-28% by weight, exceptionally preferred 20%-26% by weight, relating respectively to the total composition.

The composition of the stick according to the invention additionally contains at least one deodorant and/or antiperspirant active substance.

Deodorant Substances.

Deodorant substances preferred according to the invention are odor absorbers, deodorizing ionic exchangers, germ inhibiting agents, pre-biotic components as well as enzyme inhibitors or, particularly preferred, combinations of the named substances.

Silicates serve as odor absorbers which simultaneously advantageously support the rheological characteristics of the composition according to the invention. Among the particularly advantageous silicates according to the invention are above all layered silicates and among these in particular montmorillonite, kaolinite, ilite, beidellite, nontronite, saponite, hectorite, bentonite, smectite and talcum. Further advantageous odor absorbers are, for example, zeolith, zincricinoleate, cyclodextrine, and certain metallic oxides such as e.g., aluminum oxide as well as chlorophyll. They are preferably used in a quantity of 0.1%-10% by weight, particularly preferred 0.5%-7% by weight and exceptionally preferred 1%-5% by weight, relating respectively to the total composition.

By germ inhibiting or anti-microbial substances in the context of the invention are meant such substances which reduce the number resp. growth of odor engendering germs inhabiting the skin. Among these germs are among others various species of the group of staphylococci, and of the groups coryne bacteria, anaerococci and micrococci.

Preferred as germ inhibiting or anti-microbial substances according to the invention are in particular organo-halogen compounds as well as halogenides, quaternary ammonium compounds, a series of vegetable extracts and zinc compounds. Among these are among others triclosan, chlorhexidine and chlorhexidine gluconate, 3,4,4'-trichlorcarbanilide, brom-chlorophene, dichlorophene, chlorothymol, chloroxylenol, hexachlorophene, dichloro-m-xylenol, dequalinium chloride, domiphene bromide, ammonium phenolsulfonate, benzalconium halogenides, benzalconium cetylphosphate, benzalconium saccharinate, benzethonium chloride, cetylpyridinium chloride, laurylpyridinium chloride, laurylisoquinolinium bromide, methylbenzedonium chloride. Further usable are phenol, phenoxyethanol, dinatrium-dihydroxyethylsulfo-succinyl-undecylenate, sodium bicarbonate, zinc lactate, sodium phenolsulfonate and zinc phenolsulfonate, ketoglutar acid, terpen alcohols such as e.g., farnesol, chlorophylline copper complexes, α-mono-alkylglycerine ethers with a branched or linear saturated or unsaturated, optionally hydroxylated $C_6$-$C_{22}$-alkyl residue, particularly preferred α-(2-ethylhexyl) glycerine ethers, commercially available as Sensiva® SC 50 (ex Schülke & Mayr), carboxylic acid esters of the mono-, di- and tri glycerines (e.g., glycerine monolaurate, diglycerine monocaprinate), lantibiotics as well as vegetable extracts (e.g., green tea and parts of linden blossom oil).

Further preferred deodorant substances are chosen from so-called prebiotic components, by which such components in the context of the invention are meant that inhibit only or at least preponderantly the odor engendering germs of the skin microflora, but not the desired, i.e., the non-odor engendering germs which belong to healthy skin flora. Explicitly included here are the substances that are described in the publications DE 10333245 and DE 10 2004 011 968 as prebiotic in effect; among these are coniferous extracts, in particular of the group of the pinaceae, and vegetable extracts of the group of Sapindaceae, Araliaceae, Lamiaceae and Saxifragaceae, in particular extracts of *Picea* spp., *Paullinia* sp., *Panax* sp., *Lamium album* or *Ribes nigrum* as well as mixtures of these substances.

Further preferred deodorant substances are chosen from germ inhibiting perfumed oils and deosafe perfumed oils, which are available from the firm Symrise, formerly Haarmann and Reimer.

Among the enzyme inhibitors are substances that inhibit the enzymes responsible for decomposition of sweat, in particular arylsulfatase, β-glucuronidase, aminoacylase, esterases, lipases and/or lipoxigenase e.g., trialkyl-citric acid esters, in particular triethyl-citrate, or zinc glycinate.

Preferred deodorant or antiperspirant sticks according to the invention are those wherein at least one deodorant active substance is chosen from arylsulfatase inhibitors, β-- Glucuronidase inhibitors, aminoacylase inhibitors, esterase inhibitors, lipase inhibitors and lipoxigenase inhibitors, α-monoalkylglycerine ethers with one branched or linear saturated or unsaturated, optionally hydroxylated $C_6$-$C_{22}$-alkyl residue, in particular α-(2-ethylhexyl) glycerine ether, phenoxyethanol, germ inhibiting perfumed oils, deosafe perfumed oils, prebiotic components, trialkyl citric acid esters, in particular triethylcitrate, substances that reduce the number of odor generating skin bacteria of the group of staphylococci, coryne bacteria, anaerococci and micrococci resp. inhibit their growth, zinc compounds, in particular zinc-phenolsulfonate and zinc ricinoleate, organo-halogen compounds, in particular triclosan, chlorhexidine, chlorhexidine gluconate and benzalconium halogenides, quaternary ammonium compounds, in particular cetylpyridiniumchloride, odor absorbers, in particular silicates and zeolithes, sodium bicarbonate, lantibiotics, as well as mixtures of the substances mentioned above.

Further preferred deodorant or antiperspirant sticks according to the invention are those wherein at least one deodorant active substance is contained in a total quantity of 0.1%-10% by weight, preferably 0.2%-7% by weight, particularly preferred 0.3%-5% by weight and exceptionally preferred 0.4%-1.0% by weight, related to the total weight of the active substance in the total composition.

Antiperspirant Active Substances.

Preferred deodorant or antiperspirant sticks according to the invention are those wherein at least one antiperspirant active substance, chosen from the water soluble astringent inorganic and organic salts of aluminum, zirconium and zinc resp. desired mixtures of these salts is contained. Particularly preferred antiperspirant active substances are chosen from aluminum chlorhydrates, in particular the aluminum chlorhydrates with the general formula $[Al_2(OH)_5Cl-2-3H_2O]_n$ that can exist in the non-active or the active (depolymerized) form, further aluminum sesquichlorhydrate, aluminum chlorhydrex-propylene glycol (PG) or -polyethylene glycol (PEG), aluminum sesquichlorhydrex-PG or —PEG, aluminum-PG-dichlorhydrex or aluminum-PEG-dichlorhydrex, aluminum hydroxide, further chosen from the aluminum zirconium chlorhydrates, such as aluminum zirconium trichlorhydrate, aluminum zirconium tetrachlorhydrate, aluminum zirconium pentachlorohydrate, aluminum zirconium octachlorohydrate, the aluminum-zirconium-chlorohydrate-glycine complexes such as aluminum zirconium trichlorohydrexglycine, aluminum zirconium tetrachlorohydrexglycine, aluminum zirconium pentachlorohydrexglycine, aluminum zirconium octachlorohydrexglycine, potassium aluminum sulfate (KAl $(SO_4)_2.12H_2O$, Alaun), aluminum undecylenoyl collagen amino acid, sodium aluminum lactate+aluminum sulfate, sodium aluminum chlorohydroxylactate, aluminum bromhydrate, aluminum chloride, the complexes of zinc and sodium salts, the complexes of lanthan and cer, the aluminum salts of lipo amino acids, aluminum sulfate, aluminum lactate, aluminum chlorohydroxyallantoinate, sodium-aluminum-chlorhydroxylactate, zinc chloride, zinc sulfocarbolate, zinc sulfate and zirconium chlorhydrate. In the context of the invention by water solubility a solubility of at least 5% by weight at 20° C. is to be understood, that means that quantities of at least 5 g of the antiperspirant active substances are soluble in 95 g water at 20° C. The antiperspirant active substances can be used as aqueous solutions.

Particularly preferred deodorant or antiperspirant sticks according to the invention are those wherein at least one antiperspirant active substance is contained in a quantity of 3%-27% by weight, preferably 5%-22% by weight and in particular 10%-20% by weight, related to the total weight of the active substance in the total composition. In a particularly preferable version the composition contains the combination of an astringent aluminum salt, in particular aluminum chlorohydrate, which, for example, is sold in powder form as Micro Dry® Ultrafine from Reheis, in the form of an aqueous solution as Locron® L from Clariant, as Chlorhydrol®, as well as in active form as Reach® 501 from Reheis. A certain aluminum sesquichlorohydrate from Reheis is offered under the name Reach® 301, which is similarly particularly preferred. Also the use of aluminum-zirconium-tetrachlorohydrex-glycine complexes, which, for example, are commercially available under the name Rezal® 36G, can be particularly preferred in the context of the invention.

The stick compositions according to the invention can contain, in a further particularly preferred version, at least one deodorant as well as also at least one antiperspirant active substance.

Low Melting Point Lipid or Wax Components

Particularly preferred deodorant or antiperspirant sticks are those wherein at least one lipid or wax component with a melting point in the range of 25°-<50° C., chosen from coconut fatty acid glycerine mono-, di- and tri-esters, butyrospermum parkii (Shea Butter) and esters of saturated, monohydric $C_8$-$C_{18}$ alcohols with saturated $C_{12}$-$C_{18}$ monocarboxylic acids, as well as mixtures of these substances, is contained. These low melting point lipid or wax components enable an optimizing of the consistency of the product and a minimizing of the visible residues on the skin. Particularly preferred are commercial products with the INCI designation Cocoglycerides, in particular the commercial products Novata (ex Cognis), particularly preferred Novata® AB, a mixture of $C_{12}$-$C_{18}$-mono-, di- and triglycerides, which melts in the range of 30-32° C., as well as the products of the Softisan line (Sasol Germany GmbH) with the INCI designation Hydrogenated Cocoglycerides, in particular Softisan 100, 133, 134, 138, 142. Further preferable esters of saturated, monohydric $C_{12}$-$C_{18}$ alcohols with saturated $C_{12}$-$C_{18}$ monocarboxylic acids are stearyl laurate, cetearyl stearate (e.g., Crodamol® CSS), cetylpalmitate (e.g., Cutina® CP) and myristylmyristate (e.g., Cetiol® MM).

Further particularly preferred deodorant or antiperspirant sticks contain at least one lipid or wax component is contained with a melting point in the range of 25°-<50° C. in quantities of 0.01% to 20% by weight, a preferable 3%-20% by weight, a particularly preferred 5%-18% by weight and an exceptionally preferred 6%-15% by weight, related to the total composition.

Fillers.

Particularly preferred deodorant or antiperspirant sticks according to the invention are those which further contain at least one solid, water-insoluble, particulate filler for the improvement of the consistency of the stick and the sensory characteristics. In an exceptionally preferred version this filler is chosen from starches, which may be modified optionally (e.g., of corn, rice, potatoes) and starch derivatives, which are pre-gelatinized if desired, in particular aluminium starch octenyl succinate, available under the name DRY FLO®, and similar starch derivatives, cellulose and cellulose derivatives, silicon dioxide, silicic acids, e.g., Aerosil®-types, spherical polyalkylsesquisiloxan particles (in particular Aerosil® R972 and Aerosil® 200V from Degussa), silicic gels or silica, talcum, kaolin, clays, e.g., bentonites, magnesium aluminum silicates, bornitride, lactoglobuline derivatives, e.g., sodium-$C_{8-16}$ isoalkylsuccinyl lactoglobulin sulfonate, available from Brooks Industries as the commercial product Biopol® OE, glass powders, polymer powders, in particular of polyolefins, polycarbonates, polyurethanes, polyamides, e.g., nylon, polyesters, polystyrenes, polyacrylates, (meth)acrylate- or (meth)acrylate-vinylidene-copolymers, which can be cross-linked, or silicones, as well as mixtures of these substances.

Polymer powders based on a polymethacrylate-copolymer are available, for example, as the commercial product Polytrap® 6603 (Dow Corning). Other polymer powders, e.g., based on polyamides, are available under the name Orgasol® 1002 (polyamide-6) and Orgasol® 2002 (polyamide-12) from Elf Atochem. Further polymer powders that are suitable for the purposes of the invention are, for example, polymethacrylate (Micropearl® M from SEPPIC or Plastic Powder A from NIKKOL), styrene-divinylbenzene-copolymers (Plastic Powder FP from NIKKOL), polyethylene- and polypropylene powders (ACCUREL® EP 400 from AKZO) or also silicone polymers (silicone powder X2-1605 from Dow Corning).

Particularly preferred deodorant or antiperspirant sticks according to the invention are those which contain at least one solid, water-insoluble, particulate filler in a total quantity of 0.01% to 30% by weight, preferably 5%-20% by weight, a particularly preferred 8%-15% by weight, relating respectively to the total composition.

Scents.

Particularly preferred deodorant or antiperspirant sticks according to the invention are those which further contain at least one scent component. As scent components perfumes, perfumed oils or perfume oil parts can be used. Perfumed oils resp. scents can be in the context of the invention individual compounds of odorous substances, e.g., the synthetic products of the type of esters, ethers, aldehydes, ketones, alcohols and hydrocarbons. Odorous substance compounds of the type of esters are e.g., benzyl acetate, phenoxyethylisobutyrate, p-tert.-butylcyclohexylacetate, linalyl acetate, dimethylbenzylcarbinyl acetate (DMBCA), phenylethylacetate, benzyl acetate, ethylmethylphenylglycinate, allylcyclohexylpropionate, styr allyl propionate, benzyl salicylate, cyclohexylsalicylate, floramate, melusate and jasmecyclate. Among the ethers are, for example, benzylethylether and ambroxan, among the aldehydes e.g., the linear alkanales with 8-18 C atoms, citral, citronellal, citronellyloxy-acetaldehyde, cyclamenaldehyde, lilial and bourgeonal, among the ketones e.g., the jonones, alpha-Isomethylionone and methylcedrylketone, among the alcohols anethol, citronellol, eugenol, geraniol, linalool, phenylethylalcohol and terpineol, among the hydrocarbons primarily the terpenes such as lemons and pines. Mixtures of various odorous substances are preferably used which orchestrate a suitable perfume blend.

Such perfumed oils can also contain natural mixtures of odorous substances, such as are available from vegetable sources, e.g., pine, citrus, jasmine, patchouli, rose or ylang-ylang oil. Similarly suitable are muscatel salve oil, chamomile oil, carnation oil, melissa oil, mint oil, cinnamon leaf oil, linden blossom oil, juniper berry oil, vetiver oil, olibanum oil, galbanum oil, labdanum oil, as well as orange blossom oil, neroli oil, orange peel oil and sandalwood oil.

In order to be perceived by the senses, an odorous substance must be evanescent, whereby along with the nature of the functional groups and the structure of the chemical compound, the molar mass also plays an important role. For this reason most of the odorous substances possess molar masses up to approximately 200 Daltons, while molar masses of 300 Daltons and above represent more an exception. On the basis of the differing evanescence of odorous substances, the odor of a perfume resp. scent composed of several odorous substances changes during the vaporizing process, whereby the odorous impression are divided into the "top note," "average note resp. body" and the "end note resp. dry out." Since the sensory perception depends to a large extent on the intensity of the odor, the top note of a perfume resp. scent does not consist alone of easily evanescent compounds, while the end note consists for the most part of less evanescent i.e., more enduring odorous substances. In the composition of perfume more easily evanescent odorous substances can be bound, for example, to certain fixatives, through which their too rapid vaporization is hindered. In the following classification of odorous substances in "more easily evanescent" resp. "enduring" odorous substances, nothing is said about the impression of the odor and about whether the corresponding odorous substance is perceived as top or average note.

Enduring odorous substances that are usable in the context of the present invention are, for example, the etherizing oils such as angelica radix oil, anise oil, arnica blossom oil, basil oil, bay oil, bergamot oil, champak blossom oil, fir oil, turpentine oil, elemi oil, eucalyptus oil, fennel oil, pine needle oil, galbanum oil, geranium oil, ginger grass oil, guaiac wood oil, balsam of gurjun oil, *helichrysum*/chasteweed oil, ho oil, ginger oil, iris oil, cajeput oil, calmus oil, chamomile oil, camphor oil, canaga oil, cardamom oil, *cassia* oil, fir cone oil, balsam of kopaiva oil, coriander oil, crisped mint oil, caraway oil, cumin oil, lavender oil, lemon grass oil, lime oil, tangerine oil, melissa oil, ambrette oil, myrrh oil, carnation oil, neroli oil, niaouli oil, oliban oil, orange oil, *origanum* oil, palmarosa oil, patchouli oil, peru balsam oil, petit grain oil, pepper mint oil, pimento oil, pine oil, rose oil, rosemary oil, sandal wood oil, celery oil, lavender oil, star anise oil, turpentine oil, *thuja* oil, thyme oil, verbena oil, vetiver oil, juniper berry oil, absinthe oil, winter green oil, ylang-ylang oil, hyssop oil, cinnamon oil, cinnamon leaf oil, citronella oil, lemon oil and cypress oil.

But also the less vaporizing resp. solid odorous substances of natural or synthetic origin can be used in the context of the present invention as enduring odorous substances resp. mixtures of odorous substances, i.e., scents. Among these compounds are the compounds named in the following as well as mixtures thereof: ambrettolide, α-amylzimtaldehyde, anethol, anisaldehyde, anise alcohol, anisol, anthranil acid methylester, acetophenone, benzylacetone, benzaldehyde, benzoe acid ethylester, benzophenone, benzyl alcohol, benzylacetate, benzylbenzoate, benzylformiate, benzylvalerianate, borneol, bornylacetate, α-bromstyrol, n-decylaldehyde, n-dodecylaldehyde, eugenol, eugenolmethylether, eucalyptol, farnesol, fenchon, fenchylacetate, geranylacetate, geranylformiate, heliotropine, heptincarboxylic acid methylester, heptaldehyde, hydrochinon-dimethylether, hydroxy cinnamic aldehyde, hydroxy cinnamic alcohol, indol, iron, isoeugenol, isoeugenolmethylether, isosafrol, jasmon, camphor, carvacrol, carvon, p-cresolmethylether, cumarin, p-methoxyacetophenone, methyl-n-amylketone, methylanthranil acid methylester, p-methylacetophenone, methylchavikol, p-methylchinoline, methyl-α-naphthylketone, methyl-n-nonylacetaldehyde, methyl-n-nonylketone, muskon, β-naphtholethylether, β-naphtholmethylether, nerol, nitrobenzol, n-nonylaldehyde, nonyl alcohol, n-octylaldehyde, p-oxy-acetophenone, pentadekanolide, β-phenylethyl alcohol, phenylacetaldehyde-dimethyacetal, phenyl acetic acid, pulegone, safrol, salicylic acid isoamylester, salicylic acid methylester, salicylic acid hexylester, salicylic acid cyclohexylester, santalol, skatol, terpineol, thyme, thymol, γ-undelactone, vanilline, veratrumaldehyde, cinnamic aldehyde, cinnamic alcohol, cinnamic acid, cinnamic acid ethylester, cinnamic acid benzylester.

Among the more evanescent odorous substances are the more easily vaporizing odorous substances of natural or synthetic origin which can be used alone or in mixtures. Examples of more easily evanescent odorous substances are alkylisothiocyanates (alkyl mustard oils), butandion, lemons, linalool, linaylacetate and -propionate, menthol, menthon, methyl-n-heptenone, phellandrene, phenylacetaldehyde, terpinylacetate, citral, citronellal.

Particularly preferred deodorant or antiperspirant sticks according to the invention are those which contain at least one scent component in a total quantity of the 0.00001% to 4% by weight, preferably 0.5%-2% by weight, relating respectively to the total compositions.

Penetration Force Values.

In a further particularly preferred version the stick compositions according to the invention are characterized by a penetration force value in the range of 150-800 gram force (g-force), preferably in the range of 350-700 gram force (g-force), particularly preferred in the range of 450-650 gram force (g-force), at a penetration depth of 5.000 mm. The penetration force value represents a measure for the hardness of a stick (or even of a solid cream composition) and states with which maximum force a defined measuring probe, here a cone of stainless steel with 45° (Model TA 15), is thrust vertically (axially) into the antiperspirant mass to be measured up to a penetration depth of 5.000 mm (five point zero zero zero mm) with a penetrative speed of 2 mm/second. The measurement of the penetration force value is carried out with the TA-XT21 Texture Analyzer of the firm Stable Micro Systems (Vienna Court, Lammas Road, Godalming, Surrey GU7 1YL, England). The maximum force is shown in gram force (g-force). Here lower values characterize a softer composition; harder compositions have a higher penetration force value. Cream-type compositions are often measured with a penetration depth of 10.000 mm (ten point zero zero zero mm), in order to obtain more exact values. This depth of penetration usually cannot be measured with the harder stick masses since in this case the stick mass often begins to break. A doubling of the penetration depth means approximately a trebling up to a quadrupling of the measuring value of the maximum force. The measurements take place at ambient conditions of 30° C. and 50% relative humidity; the specimen temperature is 23° C. The measurements take place preferably 3 days and/or 4 weeks after the manufacture of the stick according to the invention.

The antiperspirant creams published in DE 199 62 878 A1 and DE 199 62 881 A1 display penetration force values of 9-15 gram force (g-force) under the measuring conditions named here.

Electrical Resistance.

The state-of-the-art water-containing sticks are almost exclusively in the form of water-in-oil emulsions or emulsions with the aqueous phase as the dispersed phase. In order to delimit the sticks according to the invention clearly and unequivocally from the state of technology, the measurement of the electrical resistance serves as a quick and reliable test, as is usual in the examinations of emulsions. An oil-in-water system due to the continual water phase displays a higher electrical conductivity and corresponding to this a lower electrical resistance than a water-in-oil system. In a further particularly preferred version, electrical resistance of a maximum of 300 kΩ characterizes the stick compositions according to the invention. Preferable is an electrical resistance of a maximum of 100 kΩ, particularly preferred of a maximum of 80 kΩ. The resistance is measured with a Voltcraft model VC820 multimeter with an automatic measuring range conversion (0-400 Ω/40MΩ (±1%+2dgt)) and two micro-tipped measuring antennae 1.0 mm of stainless steel. The distance between the electrodes is fixed through a millimeter gauge. The measurement is carried out at room temperature (22° C.). For this the micro-tipped electrodes are fixed parallel at a distance of 27.0 mm on the millimeter gauge and are connected to the resistance-measuring device. The measurement of the electrical resistance takes place directly on the water-containing antiperspirant sticks. For this the usually curved surface of the antiperspirant sticks is cleared away with a knife to the extent that a flat cross section results. Immediately following this the measuring electrodes are stuck vertically approximately 5 mm into the stick mass. The measured values of the electrical resistance are read off after 30 seconds. The cleaning of the measuring electrodes takes place with a cellulose cloth soaked in alcohol. Under the named measuring conditions tap water displays an electrical resistance of 250 kΩ, a 20% by weight aqueous aluminum chlorohydrate solution 3 kΩ and fully desalinated water 1.7 MΩ.

Further Active Ingredients.

Particularly preferred deodorant or antiperspirant sticks according to the invention contain further pigments, e.g., titan dioxide. The pigment content supports the cosmetic acceptance of the preparation on the part of the user. Further particularly preferred deodorant or antiperspirant sticks according to the invention contain the usual component parts of cosmetic preparations, e.g., coloring agents, nanospheres, preservatives and photo-protective substances, anti-oxidants, enzymes as well as conditioners. These are contained in particularly preferred deodorant or antiperspirant sticks preferably in a quantity of 0.001%-20% by weight.

Product Stabilization.

Particularly preferred deodorant or antiperspirant sticks contain at least one radical-capturing substance for the purposes of product stabilization, particularly preferred being a substance with the INCI designation Tris (tetramethyl-hydroxy-piperidinol) citrate, which, for example, is available under the commercial name Tinogard Q of the firm Ciba. Tris (tetramethylhydroxy-piperidinol) citrate is contained preferably in quantities of 0.01%-0.1%, particularly preferred being a 0.025%-0.05% by weight, relating to the total weight of the composition according to the invention.

Further particularly preferred deodorant or antiperspirant sticks contain at least one UV-filter. Here the UV filters are preferably chosen from benzotriazole derivatives, in particular 2,2'-methylene-bis-(6-(2H-benzotriazole-2-yl)-4-(1,1,3,3-tetramethylbutyl)-phenol) [Tinosorb M (Ciba)], 2,2'-methyl-bis-[6(2H-benzotriazole-2-yl)-4-(methyl)phenol] (MIXXIM BB/200 of the firm Fairmount Chemical), 2-(2'-hydroxy-3',5'-di-t-amylphenyl)benzotriazole (CAS-No.: 025973-551), 2-(2'-hydroxy-5'-octylphenyl)benzotriazole (CAS-No. 003147-75-9), 2-(2'-hydroxy-5'-methylphenyl) benzotriazole (CAS-No. 2440-22-4), 2-(2H-benzotriazole-2-yl)-4-methyl-6-[2-methyl-3-[1,3,3,3-tetramethyl-1-((trimethylsilyl)oxy]disiloxanyl)propyl]-phenol (CAS-No.: 155633-54-8) with the INCI designation drometrizole trisiloxane, 2,4-bis-{[4-(2-ethyl-hexyloxy)-2-hydroxy]-phenyl}-6-(4-methoxyphenyl)-1,3,5-triazine (INCI: bis-ethylhexyloxyphenol methoxyphenyl triazine or also aniso triazine, available as Tinosorb® S from CIBA), 2,4-bis-{[4-(3-sulfonato)-2-hydroxy-propyloxy)-2-hydroxy]-phenyl}-6-(4-methoxyphenyl)-1,3,5-triazine-sodium salt, 2,4-bis-{[4-(3-(2-propyloxy)-2-hydroxy-propyloxy)-2-hydroxy]-phenyl}-6-(4-methoxyphenyl)-1,3,5-triazine, 2,4-bis-{[4-(2-ethyl-hexyloxy)-2-hydroxy]-phenyl}-6-[4-(2-methoxyethyl-carboxyl)-phenylamino]-1,3,5-triazine, 2,4-bis-{[4-(3-(2-propyloxy)-2-hydroxy-propyloxy)-2-hydroxy]-phenyl}-6-[4-(ethylcarboxyl)-phenylamino]-1,3,5-triazine, 2,4-bis-{[4-(2-ethylhexyloxy)-2-hydroxy]-phenyl}-6-(1-methyl-pyrrol-2-yl)-1,3,5-triazin, 2,4-bis-{[4-tris(trimethylsiloxy-silylpropyloxy)-2-hydroxy]-phenyl}-6-(4-methoxyphenyl)-1,3,5-triazine, 2,4-bis-{[4-(2-methylpropenyloxy)-2-hydroxy]-phenyl}-6-(4-methoxyphenyl)-1,3,5-triazine, 2,4-bis-{[4-(1',1',1',3',5',5', 5'-heptamethylsiloxy-2-methyl-propyloxy)-2-hydroxy]-phenyl}-6-(4-methoxyphenyl)-1,3,5-triazine, as well as mixtures of the components named above. Further the addition of water-soluble UV filters is preferable. Preferred water soluble UV filters are 2-phenylbenzimidazole-5-sulfonic acid, phenylene-1,4-bis-(2-benzimidazyl)-3,3'-5,5'-tetrasulfonic acid and their alkali-, earth alkali-, ammonium-, alkylammonium-, alkanolammonium- and glucammonium salts, in particular the sulfonic acid itself with the INCI designation of phenylbenzimidazole sulfonic acid (CAS.-No. 27503-81-7), which, for example, is available under the commercial name of Eusolex 232 with Merck or under Neo Heliopan Hydro with Symrise, and the phenylene-1,4-bis-(2-benzimidazyl)-3,3'-5,5'-tetrasulfonic acid-bis-sodium salt with the INCI designation disodium phenyl dibenzimidazole tetrasulfonate (CAS-No.: 180898-37-7), which is, for example, available under the commercial name of Neo Heliopan AP with Symrise, sulfonic acid derivatives of benzophenonene, preferably 2-hydroxy-4-methoxybenzo-phenone-5-sulfonic acid and its salts and sulfonic acid derivatives of the 3-benzylidencamphor, such as e.g. 4-(2-oxo-3-bornylidenmethyl) benzol sulfonic acid.

Further particularly preferred deodorant or antiperspirant sticks contain the radical capturing agent tris (tetra-methylhydroxy-piperidinol) citrate and the UV filter bumetrizole for the purposes of product stabilization. Bumetrizole is contained preferably in quantities of 0.01%-0.1%, particularly preferred being 0.025%-0.05% by weight, relating to the total weight of the composition according to the invention.

Further particularly preferred deodorant or antiperspirant sticks contain at least one complexing substance for the purposes of product stabilization. As a complexing substance particularly preferred is ethylenediaminetetra-acetic acid (EDTA) and its sodium salts, such as are, for example, available under the commercial name of Trilon B of the firm BASF, further nitrilotri-acetic acid (NTA) and its sodium salts, β-alanindi-acetic acid and its salts and phosphonic acids and their salts. The complexing substance, at least one in number, is preferably contained in a total weight of 0.01%-0.5% by weight, particularly preferred in a 0.08%-0.2% by weight, relating to the total weight of the composition according to the invention.

Further extraordinarily preferred deodorant or antiperspirant sticks according to the invention contain at least one radical-capturing substance and at least one substance chosen from UV filters and complexing substances.

Further extraordinarily preferable deodorant or antiperspirant sticks according to the invention are characterized by the fact that they contain tris(tetramethylhydroxy-piperidinol) citrate, Bumetrizole and ethylenediaminetetraacetic acid, the latter optionally as sodium salt.

Hair Growth Inhibitors.

Further particularly preferred deodorant or antiperspirant sticks contain at least one hair-growth inhibiting substance. Suitable substances that inhibit hair-growth are in particular chosen from eflornithine, substance combinations of soya protein hydrolysate, urea, menthol, salicylic acid and extracts of *hypericum perforatum, hamamelis virginiana, arnica montana* and the bark of *Salix alba*, such as is, for example, contained in the raw material "Pilinhib® Veg LS 9109" of Laboratoires Sérobiologiques with the INCI declaration "Propylene glycol, Hydrolyzed Soy Protein, *Hypericum Perforatum* Extract, *Hamamelis Virginiana* Extract, Arnica Montana Flower Extract, Urea, *Salix Alba* Bark Extract, Menthol, Salicylic acid," further substance combinations of extracts of *Epilobium angustifolium*, the seeds of *Cucurbita pepo* (pumpkin) and the fruits of *Serenoa serrulata*, such as are, for example, and preferably contained in the raw material "ARP 100" of Greentech S.A./Rahn with the INCI declaration "Water, Alcohol, *Serenoa Serrulata* Fruit Extract, *Epilobium Angustifolium* Extract, *Cucurbita Pepo* (Pumpkin) Seed Extract," further substance combinations of xylitol and the extracts of Citrus medica limonum (lemon) fruit, *Carica papaya* (papaya) and olive leaves, such as are contained, for example, and preferably in the raw material "Xyleine" from Impag/Seporga with the INCI declaration "Xylitol and Citrus Medica Limonum (Lemon) Fruit Extract and *Carica Papaya* (Papaya) Fruit Extract and *Olea europaea* (olive) leaf extract," further substance combinations of *Humulus lupulus, Viscum album, Salvia officinalis, Carica papaya* and *Thuya occidentalis*, such as are contained, for example, and preferably in the raw material Plantafluid Complex AH of the firm Plantapharm with the INCI declaration "Aqua, Propylene Glycol, *Humulus Lupulus, Viscum Album, Salvia Officinalis, Carica Papaya, Thuya Occidentalis*," as well as extracts of *Larrea divaricata*, such as are contained, for example, and preferably in the raw material Capislow from Sederma, which contains lecithin vesicles with a hydroglycolized extract of *Larrea divaricata*.

The preferred compositions according to the invention contain at least one of the hair-growth inhibiting substances preferably in a quantity of 0.1%-10% by weight, preferably 0.5%-5% by weight and particularly preferred 1%-4% by weight, related respectively to the weight of the raw material tel quel and the total weight of the combination according to the invention.

Preservatives.

Preferably, the usual preservatives can also be added to the compositions according to the invention, in order to prevent the decomposition of the product through microbial growths. Numerous preservatives also necessarily have deodorizing characteristics, so that some substances belong to both groups. For cosmetics preferably suitable as preservatives are, for example, benzoic acid and its derivatives (e.g., propyl-, phenyl- and butylbenzoate, ammonium-, sodium-, potassium- and magnesiumbenzoate), propionic acid and its derivatives (e.g., ammonium-, sodium-, potassium- and magnesium propionate), salicylic acid and its derivatives (e.g., sodium-, potassium- and magnesiumsalicylate), 4-hydroxybenzoic acid and its esters and alkali-metal salts (e.g., methyl-, ethyl-, propyl-, isopropyl-, butyl-, isobutyl-, isodecyl-, phenyl-, phenoxyethyl- and benzylparabens, hexamidine parabens and di-parabens, sodium and potassium parabens, sodium and potassium methylparabens, potassium butylparabens, sodium and potassium propylparabens), alcohols and their salts (e.g., ethanol, propanol, isopropanol, benzyl alcohol, phenethyl alcohol, phenol, potassium phenolate, phenoxyethanol, phenoxyiso-propanol, o-phenylphenol), guajacol and its derivatives, chlorhexidine and its derivatives (e.g., chlorhexidindiacetate, -digluconate, and -dihydrochloride), hydantoin and its derivatives (e.g., DEDM- and DMDM-hydantoin, DEDM-Hydantoindilaurate), urea and urea derivatives (e.g., diazolidinyl urea, imidazolidinyl urea), ferulaic acid and its derivatives (e.g., ethylferulate), sorbinic acid and its derivatives (e.g., isopropylsorbate, TEA-sorbate, sodium-, potassium- and magnesiumsorbate), isothiazol and oxazol derivatives (e.g., methylisothiazolinone, methylchloroisothiazolinone, di-methyloxazolidine), quaternary ammonium compounds (e.g., Polyquaternium-42, Quaternium-8, Quaternium-14, Quaternium-15), carbamates (e.g., iodopropynylbutylcarbamate), formaldehyde and sodium formate, glutaraldehyde, glyoxal, hexamidine, dehydracetic acid, 2-bromo-2-nitropropane-1,3-diol, isopropylkresol, methyldibromoglutaronitrile, polyaminopropylbiguanide, sodium hydroxymethylglycinate, sodium phenolsulfonate, triclocarban, triclosan, zinc pyrithione, as well as diverse peptide antibiotics (e.g., Nisine).

Preferred preservatives according to the invention are phenoxyethanol, the esters of 4-hydroxybenzoic acid, in particular methyl-, ethyl-, propyl-, isopropyl-, butyl- and iso-butylparabens, as well as iodopropynylbutylcarbamate.

The quantity of the preservatives in the combinations preferred according to the invention is 0.001%-10% by weight, preferably 0.1%-5% by weight and in particular 0.1%-3% by weight, relating to the total weight of the combination.

In principle, the subject of the present invention is to be extended to other cosmetic stick combinations which do not represent deodorant or antiperspirant sticks. A content of deodorant or antiperspirant active substances is not obligatory in such sticks. Corresponding sticks, for example, can be mass-produced as lipsticks or concealer sticks and used through topical application on the skin.

A further subject of the present invention is a cosmetic, non-therapeutic process in order to minimize body odor, wherein a cosmetic deodorant and/or antiperspirant composition according to one of the patent claims 1 to 18 is to be applied on the skin, in particular on the skin of the armpits.

A further subject of the present invention is a process for the manufacture of a deodorant or antiperspirant stick according to one of the claims 1 to 18, whereby the wax and oil components are heated up to 90°-95° C. and melted down along with the oil-in-water and the water-in-oil emulsifier(s), following which the water, which has similarly been heated to 90°-95° C. along with the water-soluble effective components is added, while being thoroughly stirred, further contents, optionally, are mixed in, the mixture is cooled to a suitable temperature for filling, is filled in suitable dispensers and solidified through static cooling (without being further stirred) at room temperature.

The following examples are meant to clarify the subject of the invention without limiting it only to these.

TABLE 2

Exemplary Compositions/Combinations According to the Invention.

| Components | Example No. | | | | | | | | | |
|---|---|---|---|---|---|---|---|---|---|---|
| | 1 | 2 | 3 | 4 | 5 | 6 | 7 | 8 | 9 | 10 |
| Cutina ® AGS | 2.5 | — | — | 2.5 | 2.5 | 2.5 | 2.5 | 2.5 | 2.5 | 2.5 |
| Cutina ® EGMS | — | 2.5 | — | — | — | — | — | — | — | — |
| Cutina ® PES | — | — | 2.5 | — | — | — | — | — | — | — |
| Cutina ® FS45 | 3.5 | 3.5 | 3.5 | 3.5 | 3.5 | 3.5 | 3.5 | 2.6 | 2.6 | 2.6 |
| Eumulgin ® B2 | 0.8 | 0.8 | 0.8 | 0.8 | 0.8 | 0.8 | 0.8 | 0.8 | 0.8 | 0.8 |
| Eumulgin ® B3 | 0.8 | 0.8 | 0.8 | 0.8 | 0.8 | 0.8 | 0.8 | 0.8 | 0.8 | 0.8 |
| Di-isopropyladipate (Ceraphyl ® 230) | 6 | 6 | 6 | 6 | 6 | 6 | 6 | 6 | 6 | 6 |
| Novata ® AB | 4 | 4 | 4 | 4 | 4 | 4 | 4 | 4 | 4 | 4 |
| Cutina ® CP | 5 | 5 | 5 | 5 | 5 | 5 | 5 | 5 | 5 | 5 |
| Cutina ® HR | 4 | 4 | 4 | 4 | 4 | 4 | 4 | 4 | 4 | 4 |
| Kester wax K62 | 5 | 5 | 5 | 4 | 2.5 | 5 | 4 | 5 | 4 | 5 |
| Locron ® L (50% ACH solution) | 40 | 40 | 40 | 40 | 40 | — | — | 40 | 40 | — |
| Rezal 36 (46%) GC Solution | — | — | — | — | — | 47.4 | 48.4 | — | — | 47.4 |
| Talcum Pharma G | 10 | 10 | 10 | 10 | 10 | 10 | 10 | 10 | 10 | 10 |
| Perfume | 1 | 1 | 1 | 1 | 1 | 1 | 1 | 1 | 1 | 1 |
| 1,2 propanediol | 10 | 10 | 10 | 10 | 10 | 10 | 10 | 10 | 10 | 10 |
| Water, fully desalinated | 7.4 | 7.4 | 7.4 | 8.4 | 9.9 | — | — | 8.3 | 9.3 | 0.9 |
| Total | 100.0 | 100.0 | 100.0 | 100.0 | 100.0 | 100.0 | 100.0 | 100.0 | 100.0 | 100.0 |
| Tactile solidity of the mass (sensory) | solid | solid | solid | solid | solid | solid | solid | solid | solid | solid |
| Solubility parameter oil [(cal/cm$^3$)$^{0.5}$] | 8.46 | 8.46 | 8.46 | 8.46 | 8.46 | 8.46 | 8.46 | 8.46 | 8.46 | 8.46 |
| Solubility parameter W/O emulsifier [(cal/cm$^3$)$^{0.5}$] | 8.24 | 8.28 | 8.00-8.20 | 8.24 | 8.24 | 8.24 | 8.24 | 8.24 | 8.24 | 8.24 |
| Difference, solubility parameter [(cal/cm$^3$)$^{0.5}$] | 0.22 | 0.18 | 0.36 | 0.22 | 0.22 | 0.22 | 0.22 | 0.22 | 0.22 | 0.22 |

All quantities are provided in % by weight.

TABLE 3

Comparative Examples.

| Components | Example No. | | |
|---|---|---|---|
| | C 1 | C 2 | C 3 |
| Cutina ® ACS | 2.5 | 2.5 | — |
| Cutina ® EGMS | — | — | 2.5 |
| Cutina ® PES | — | — | — |
| Cutina ® FS45 | 3.5 | 3.5 | 3.5 |
| Eumulgin ® B2 | 0.8 | 0.8 | 0.8 |
| Eumulgin ® B3 | 0.8 | 0.8 | 0.8 |
| Di-isopropyladipate (Ceraphyl ® 230) | — | — | — |
| Nexbase 2004 FG | — | 6 | 6 |
| Cetiol ® OE | 6 | — | — |
| Novata ® AB | 4 | 4 | 4 |
| Cutina ® CP | 5 | 5 | 5 |
| Cutina ® HR | 4 | 4 | 4 |
| Kester wax K62 | 5 | 5 | 5 |
| Locron ® L | 40 | 40 | 40 |
| Talcum Pharma G | 10 | 10 | 10 |
| Perfume | 1 | 1 | 1 |
| 1,2-propanediol | 10 | 10 | 10 |
| Water, fully desalinated | 7.4 | 7.4 | 7.4 |
| Total | 100.0 | 100.0 | 100.0 |
| Tactile solidity of the mass (sensory) | very soft, creamy | Soft, elastic/ plastic | very soft, creamy |
| Solubility parameter oil [(cal/cm$^3$)$^{0.5}$] | 7.3 | <7.6 | <7.6 |
| Solubility parameter W/O emulsifier [(cal/cm$^3$)$^{0.5}$] | 8.24 | 8.24 | 8.28 |
| Difference, solubility parameter [(cal/cm$^3$)$^{0.5}$] | −0.94 | −0.74 | −0.78 |

TABLE 4

Further Exemplary Combinations/Compositions According to the Invention.

| Components | 11 | 12 | 13 | 14 | 15 | 16 | 17 |
|---|---|---|---|---|---|---|---|
| Cutina ® AGS | 2.5 | 2.5 | — | — | — | 2.5 | 2.5 |
| Cutina ® EGMS | — | — | 2.5 | 2 | — | — | — |
| Cutina ® PES | — | — | — | — | 2 | — | — |
| Cutina ® FS45 | 3.5 | 3.5 | 3.5 | 3.5 | 3.5 | 3.5 | 3.5 |
| Eumulgin ® B2 | 0.8 | 0.8 | 0.8 | 0.8 | 0.8 | 0.8 | 0.8 |
| Eumulgin ® B3 | 0.8 | 0.8 | 0.8 | 0.8 | 0.8 | 0.8 | 0.8 |
| Di-isopropyladipate (Ceraphyl ® 230) | 6 | 6 | 6 | 6 | 6 | 6 | 6 |
| Novata ® AB | 4 | 4 | 4 | 4 | 4 | 4 | 4 |
| Cutina ® CP | 5 | 5 | 5 | 5 | 5 | 5 | 5 |
| Cutina ® HR | 4 | 4 | 4 | 4 | 4 | 4 | 4 |
| Kester wax K62 | 5 | 5 | 5 | 5 | 5 | 5 | 5 |
| Locron ® L (50% ACH solution) | 40 | 40 | 40 | 40 | 40 | 40 | 40 |
| Talcum Pharma G | 10 | 10 | 10 | 10 | 10 | 10 | 10 |
| Perfume | 1.2 | 1.2 | 1.2 | 1.2 | 1.2 | 1.2 | 1.2 |
| Sensiva SC 50 | 0.75 | 0.5 | 0.6 | 0.6 | 0.6 | 0.6 | 0.6 |
| Tinogard Q | 0.025 | 0.05 | 0.025 | — | 0.1 | 0.1 | — |
| Tinogard AS | — | — | 0.025 | — | — | — | — |
| 1,2-propanediol | 10 | 10 | 10 | 10 | 10 | 10 | 10 |
| Water, fully desalinated | 6.425 | 6.65 | 6.55 | 7.1 | 7 | 6.5 | 6.6 |
| Total | 100.0 | 100.0 | 100.0 | 100.0 | 100.0 | 100.0 | 100.0 |
| Tactile solidity of the mass (sensory) | solid | solid | solid | solid | solid | solid | solid |
| Solubility parameter oil [(cal/cm$^3$)$^{0.5}$] | 8.46 | 8.46 | 8.46 | 8.46 | 8.46 | 8.46 | 8.46 |
| Solubility parameter W/O emulsifier [(cal/cm$^3$)$^{0.5}$] | 8.24 | 8.24 | 8.28 | 8.28 | 8.0-8.2 | 8.24 | 8.24 |
| Difference, solubility parameter [(cal/cm$^3$)$^{0.5}$] | 0.22 | 0.22 | 0.18 | 0.18 | 0.36 | 0.22 | 0.22 |
| Water content | 26.425 | 26.65 | 26.55 | 27.1 | 27 | 26.5 | 26.6 |

Raw Materials Used.

| Components | INCI | Supplier/Manufacturer |
|---|---|---|
| Cetiol ® OE | Dioctyl Ether | Cognis |
| Cutina ® AGS | Glycol Distearate | Cognis |
| Cutina ® EGMS | Glycol Stearate | Cognis |
| Cutina ® PES | Pentaerythrityl Distearate | Cognis |
| Cutina ® CP | Cetyl Palmitate | Cognis |
| Cutina ® FS45 | Palmitic Acid, Stearic Acid | Cognis |
| Cutina ® HR | Hydrogenated Castor Oil | Cognis |
| Eumulgin ® B2 | Ceteareth-20 | Cognis |
| Eumulgin ® B3 | Ceteareth-30 | Cognis |
| Eutanol ® G | Octyldodecanol | Cognis |
| Kester wax K80 H | C20-40 Alkyl Stearate | Koster Keunen |
| Kester wax K62 | Cetearyl Behenate | Koster Keunen |
| Locron L (50% ACH solution) | Aluminum Chlorohydrate | Clariant |
| Nexbase 2004 FG | Hydrogenated Polydecene | Fortum |
| Novata ® AB | Cocoglycerides | Cognis |
| Rezal ® 36 GC solution (46%) | Aluminum Zirconium Tetra-chlorohydrex Gly | Reheis |
| Sensiva SC 50 | Ethylhexyloxyglycerin | Schülke & Mayr |
| Talcum Pharma G | Talcum | Erbslöh |
| Tinogard AS | Bumetrizole | Ciba |
| Tinogard Q | Tris (tetramethylhydroxy-piperidinol) citrate | Ciba |

All quantities are provided in % by weight.

The invention claimed is:

1. A deodorant or antiperspirant stick composition comprising:
   a) 4%-20% of at least one lipid or wax component with a melting point >50° C., which is not to be apportioned to components b) or c),
   b) 0.5%-10% of at least one nonionic oil-in-water emulsifier with an HLB value of more than 7 within an oil-in-water emulsifier mixture with an average HLB value in the range of 10-19,
   c) 1%-4% of at least one nonionic water-in-oil emulsifier with an HLB value of more than 1.0 and up to 7.0, chosen from the mono- and di-esters of ethylene glycol and the mono -,di-,tri- and tetra esters of pentaerythritol with linear saturated and unsaturated fatty acids with 12-30 carbon atoms, which can be hydroxylated, as well as mixtures thereof, as consistency providers and/or water binders,
   d) 3%-20% of at least one oil, liquid at 20° C., which represents neither a scent component nor an essential oil, whereby the average solubility parameter of the totality of the contained oils differs in the presence of linear saturated fatty alcohols with a chain length of at least 8 carbon atoms by a maximum of $-0.7$ $(cal/cm^3)^{0.5}$ or a maximum of $+0.7$ $(cal/cm^3)^{0.5}$ and in the presence of water-in-oil emulsifiers, which are different from linear saturated fatty alcohols with a chain length of at least 8 carbon atoms, linear saturated fatty alcohols with a chain length of at least 8 carbon atoms being absent, by a maximum of $-0.4$ $(cal/cm^3)^{0.5}$ or a maximum of $+0.7$ $(cal/cm^3)^{0.5}$ from the average solubility parameter of the water-in-oil emulsifier(s), wherein the composition contains no silicon oils and/or hydrocarbons, e) at least one water-soluble polyhydric $C_2$-$C_9$-alkanol with 2-6 hydroxyl groups and/or at least one water-soluble polyethylene glycol with 3-20 ethylene oxide units, f) 5% up to less than 50% by weight of water, and g) at least one deodorant or antiperspirant active substance, wherein the composition is an oil-in-water dispersion/emulsion in the form of a stick, all weight percentages based on total weight of the composition unless indicated otherwise.

2. The deodorant or antiperspirant stick composition according to claim 1, wherein the lipid or wax component a) is at least an ester(s) of a saturated, monohydric $C_{16}$-$C_{60}$-alkanol and/or a saturated $C_8$-$C_{36}$-monocarboxylic acid present in an amount of 2%-1 0% by weight of the total composition.

3. The deodorant or antiperspirant stick composition according to claim 1, further comprising at least two nonionic water-in-oil emulsifiers having I-ILB values of more than 1.0 and up to 7.0.

4. The deodorant or antiperspirant stick composition according to claim 1, wherein the oils d), liquid at 20° C., contain a maximum of 20% by weight of oil(s) related to the total weight of oils liquid at 20° C., the solubility parameter of which differs by more than $-0.4$ resp. $-0.7$ $(call cm^3)^{0.5}$ or by more than $+0.7$ $(cal/cm^3)^{0.5}$ from the (average) solubility parameter of the water-in-oil emulsifier(s).

5. The deodorant or antiperspirant stick composition according to claim 1, wherein oils liquid at 20° C. are contained, the solubility parameter of which differs by more than $\pm 1.0$ $(cal/cm^3)^{0.5}$ from the average solubility parameter of the water-in-oil emulsifier(s).

6. The deodorant or antiperspirant stick composition according to claim 1, wherein the water-soluble polyhydric $C_2$-$C_8$ alkanol with 2-6 hydroxyl groups and/or the water-soluble polyethylene glycol with 3-20 ethylene oxide units is contained in all in quantities of 3%-30% by weight in the composition.

7. The deodorant or antiperspirant stick composition according to claim 1, further comprising at least one lipid or wax component with a melting point in the range of 25° to <50° C.

8. The deodorant or antiperspirant stick composition according to claim 7, wherein the lipid or wax component with a melting point in the range of 25° -<50° C. is contained in quantities of 0.01% to 20% by weight of the total composition.

9. The deodorant or antiperspirant stick composition according to claim 1, which has a penetration force value in the range of 150-800 gram force at a penetration depth of 5.000 mm.

10. The stick composition according to claim 1, which has an electrical resistance of a maximum of 300 k$\Omega$.

11. The deodorant or antiperspirant stick composition according to claim 1, wherein the deodorant or antiperspirant active substance is selected from the group consisting of arylsulfatase inhibitors,β-glucuronidase inhibitors, aminoacylase inhibitors, esterase inhibitors, lipase inhibitors and lipoxigenase inhibitors, α-monoalkyl glycerine ethers with one-branched or linear saturated or unsaturated, optionally hydroxylated $C_6$-$C_{22}$ alkyl residue, and α-(2ethylhexyl) glycerine ether, phenoxy-ethanol, perfumed germ inhibiting oils, deosafe perfumed oils, components with pre-biotic action, trialkylcitric acid esters, triethylcitrate, substances, which reduce the number of the odor causing skin bacteria of the group of staphylococci, coryne bacteria xerosis, coryne bacterium, anaerococci and micrococci, or which inhibit their growth, zinc compounds, zinc phenolsulfonate and zinc ricinoleate, organo-halogen compounds, triclosan, chlorhexidine, chlorhexidine gluconate and benzalkonium halogenides, quaternary ammonium compounds, cetylpyridinium chloride, odor absorbers, silicates and zeolites, sodium bicarbonate, antibiotics, and mixtures of the substances named above, and/or the antiperspirant active substance is chosen from the water-soluble, astringent, inorganic and organic salts of aluminum, zirconium and zinc, or any mixtures of these salts.

12. The deodorant or antiperspirant stick composition according to claim 1, which further contains at least one solid, water-insoluble particulate filler.

13. The deodorant or antiperspirant stick composition according to claim 1, which contains 10% to less than 30% by weight of water.

14. The deodorant or antiperspirant stick composition according to claim 1, wherein the total content of nonionic and ionic emulsifiers and/or surfactants with an HLB value of over 8 is a maximum 20% by weight of the total composition of the invention.

15. The deodorant or antiperspirant stick composition according to claim 1, further containing at least one complexing substance.

16. The deodorant or antiperspirant stick composition according to claim 1, further containing at least one hair-growth inhibiting substance.

17. A cosmetic, non-therapeutic process for the reduction of body odor, comprising the step of applying to the skin the deodorant or antiperspirant stick composition according to claim 1.

18. A process for the manufacture of a deodorant or antiperspirant stick composition according to claim 1 comprising the steps of:

1) heating components a), b), c) and d) to between 90-95° C., thereby melting those components, 2) adding to the melted components a), b), c) and d) components e), f) and g), which are also heated to 90-95° C.;

3) stirring the components during and after the addition step (2) to form a mixture;

4) filling dispensers with the mixture; and 5) allowing the filled mixture to cool and solidify.

* * * * *